US010829562B2

(12) United States Patent
Vanhoorelbeke et al.

(10) Patent No.: US 10,829,562 B2
(45) Date of Patent: Nov. 10, 2020

(54) HAEMORRHAGIC DISORDER DUE TO VENTRICULAR ASSIST DEVICE

(71) Applicant: KATHOLIEKE UNIVERSITEIT LEUVEN, Leuven (BE)

(72) Inventors: Karen Vanhoorelbeke, Zwevegem (BE); Shannen Deconinck, Avelgem (BE); Hendrik Feys, Zwevegem (BE); An-Sofie Schelpe, Zwevegem (BE)

(73) Assignee: KATHOLIEKE UNIVERSITEIT LEUVEN, Leuven (BE)

( * ) Notice: Subject to any disclaimer, the term of this patent is extended or adjusted under 35 U.S.C. 154(b) by 120 days.

(21) Appl. No.: 16/061,116

(22) PCT Filed: Dec. 8, 2016

(86) PCT No.: PCT/EP2016/080229
§ 371 (c)(1),
(2) Date: Jun. 11, 2018

(87) PCT Pub. No.: WO2017/097889
PCT Pub. Date: Jun. 15, 2017

(65) Prior Publication Data
US 2018/0362665 A1 Dec. 20, 2018

Related U.S. Application Data

(60) Provisional application No. 62/265,868, filed on Dec. 10, 2015.

(51) Int. Cl.
*C07K 16/40* (2006.01)
*A61K 39/395* (2006.01)

(52) U.S. Cl.
CPC .......... *C07K 16/40* (2013.01); *A61K 39/3955* (2013.01); *C07K 2317/33* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,946,778 A | 8/1990 | Ladner et al. |
| 5,091,513 A | 2/1992 | Huston et al. |
| 5,223,409 A | 6/1993 | Ladner et al. |
| 5,258,498 A | 11/1993 | Huston et al. |
| 5,260,203 A | 11/1993 | Ladner et al. |
| 5,403,484 A | 4/1995 | Ladner et al. |
| 5,427,908 A | 6/1995 | Dower et al. |
| 5,455,030 A | 10/1995 | Ladner et al. |
| 5,516,637 A | 5/1996 | Huang et al. |
| 5,571,698 A | 11/1996 | Ladner et al. |
| 5,580,717 A | 12/1996 | Dower et al. |
| 5,658,727 A | 8/1997 | Barbas et al. |
| 5,698,426 A | 12/1997 | Huse |
| 5,733,743 A | 3/1998 | Johnson et al. |
| 5,750,753 A | 5/1998 | Kimae et al. |
| 5,780,225 A | 7/1998 | Wigler et al. |
| 5,821,047 A | 10/1998 | Garrard et al. |
| 5,969,108 A | 10/1999 | McCafferty et al. |

FOREIGN PATENT DOCUMENTS

| | | |
|---|---|---|
| EP | 0239400 B1 | 8/1994 |
| EP | 0451216 B1 | 1/1996 |
| WO | 9002809 A1 | 3/1990 |
| WO | 9110737 A1 | 7/1991 |
| WO | 9201047 A1 | 1/1992 |
| WO | 9218619 A1 | 10/1992 |
| WO | 9222324 A1 | 12/1992 |
| WO | 9311236 A1 | 6/1993 |
| WO | 9404678 A1 | 3/1994 |
| WO | 9515982 A2 | 6/1995 |
| WO | 9520401 A1 | 8/1995 |
| WO | 9749805 A2 | 12/1997 |
| WO | 2015158851 A1 | 10/2015 |

OTHER PUBLICATIONS

European Office Communication from EP Application No. 16820175.4, dated Mar. 27, 2019.
Plückthun, "Antibodies from *Escherichia coli*," Chapter 11, The Pharmacology of Monoclonal Antibodies, vol. 113, 1994, pp. 269-304.
Carter et al., "High Level *Escherichia coli* Expression and Production of a Bivalent Humanized Antibody Fragment," Bio/Technology, vol. 10, Feb. 1992, pp. 163-167.
Kettleborough et al., "Isolation of Tumor Cell-Specific Single-Chain Fv from Immunized Mice Using Phage-Antibody Libraries and the Re-Construction of Whole Antibodies from These Antibody Fragments," European Journal of Immunology, vol. 24, 1994, pp. 952-958.
Burton et al., "Human Antibodies from Combinatorial Libraries," Advances in Immunology, vol. 57, 1994, pp. 191-280.
Mullinax et al., "Expression of a Heterodimeric Fab Antibody Protein in One Cloning Step," BioTechniques, vol. 12, No. 6, 1992, pp. 864-869.
Sawai et al., "Direct Production of the Fab Fragment Derived From the Sperm Immobilizing Antibody Using Polymerase Chain Reaction and cDNA Expression Vectors," American Journal of Reproductive Immunology, vol. 34, 1995, pp. 26-34.
Huston et al., "Protein Engineering of Single-Chain Fv Analogs and Fusion Proteins," Methods in Enzymology, vol. 203, 1991, pp. 46-89.
Schaffer et al., "Bleeding Complications and Blood Product Utilization With Left Ventricular Assist Device Implementation," The Annals of Thoracic Surgery, vol. 91, 2011, pp. 740-749.
Padlan et al., "Identification of Specificity-Determining Residues in Antibodies," FASEB Journal, vol. 9, 1995, pp. 133-139.

(Continued)

*Primary Examiner* — Padmavathi Baskar
(74) *Attorney, Agent, or Firm* — Workman Nydegger

(57) ABSTRACT

The present invention relates to methods of treatment by human ADAMTS13 inhibition in circulatory assist device induced haemorrhagic complication such as a bleeding disorder, in particular, bleeding after left ventricular assist device implantation. The present invention further relates to specific monoclonal antibodies inhibiting ADAMTS13 function.

15 Claims, 13 Drawing Sheets

Specification includes a Sequence Listing.

(56) References Cited

OTHER PUBLICATIONS

Huston et al., "Protein Engineering of Antibody Binding Sites: Recovery of Specific Activity in an Anti-Digoxin Single-Chain Fv Analogue Produced in *Escherichia coli*," Proceedings of the National Academy of Sciences of the United States of America, vol. 85, Aug. 1988, pp. 5879-5883.
Nelson, "Antibody Fragments," mAbs, vol. 2, No. 1, Jan. 2010, pp. 77-83.
Pascalis et al., "Grafting of "Abbreviated" Complementarity-Determining Regions Containing Specificity-Determining Residues Essential for Ligand Contact to Engineer a Less Immunogenic Humanized Monoclonal Antibody," The Journal of Immunology, vol. 169, 2002, pp. 3076-3084.
Kashmiri et al., "SDR Grafting—a New Approach to Antibody Humanization," Methods, vol. 36, Jan. 17, 2005, pp. 25-34.
Almagro et al., "Humanization of Antibodies," Frontiers in Bioscience, vol. 13, Jan. 1, 2008, pp. 1619-1633.
Vincke et al., "General Strategy to Humanize a Carnelid Single-domain Antibody and Identification of a Universal Humanized Nanobody Scaffold," The Journal of Biological Chemistry, vol. 284, No. 5, Jan. 30, 2009, pp. 3273-3284.
Borras et al., "Generic Approach for the Generation of Stable Humanized Single-chain Fv Fragments from Rabbit Monoclonal Antibodies," The Journal of Biological Chemistry, vol. 285, No. 12, Mar. 19, 2010, pp. 9054-9066.
Harding et al., "The Immunogenicity of Humanized and Fully Human Antibodies," mAbs, vol. 2, No. 3, May 2010, pp. 256-265.
Jones et al., "Replacing the Complementarity-Determining Regions in a Human Antibody with those from a Mouse," Nature, vol. 321, May 29, 1986, pp. 522-525.
Riechmann et al., "Reshaping Human Antibodies for Therapy," Nature, vol. 332, Mar. 24, 1988, pp. 323-327.
Plückthun, "Antibody Engineering," Biotechnology, vol. 2, 1991, pp. 238-246.
Brinkmann et al., "Phage Display of Disulfide-Stabilized Fv Fragments," Journal of Immunological Methods, vol. 182, Jan. 9, 1995, pp. 41-50.
Ames et al., "Conversion of Murine Fabs Isolated from a Combinatorial Phage Display Library to Full Length Immunoglobulins," Journal of Immunological Methods, vol. 184, Mar. 20, 1995, pp. 177-186.
Persic et al., "An Integrated Vector System for the Eukaryotic Expression of Antibodies or their Fragments after Selection from Phage Display Libraries," Gene, vol. 187, 1997, pp. 9-18.
Better et al., "*Escherichia coli* Secretion of an Active Chimeric Antibody Fragment," Science, vol. 240, May 20, 1988, pp. 1041-1043.
Skerra et al., "Assembly of a Functional Immunoglobulin Fv Fragment in *Escherichia coli*," Science, vol. 240, May 20, 1988, pp. 1038-1041.
Shu et al., "Secretion of a Single-Gene-Encoded Immunoglobulin from Myeloma Cells," Proceedings of the National Academy of Sciences of the United States of America, vol. 90, Sep. 1993, pp. 7995-7999.
Yang et al., "CDR Walking Mutagenesis for the Affinity Maturation of a Potent Human Anti-HIV-1 Antibody into the Picomolar Range," Journal of Molecular Biology, vol. 254, 1995, pp. 392-403.
Vaughan et al., "Human Antibodies by Design," Nature Biotechnology, vol. 16, Jun. 1998, pp. 535-539.
Rader et al., "A Phage Display Approach for Rapid Antibody Humanization: Designed Combinatorial V Gene Libraries," Proceedings of the National Academy of Sciences of the United States of America, vol. 95, Jul. 1998, pp. 8910-8915.
Gram et al., "In Vitro Selection and Affinity Maturation of Antibodies from a Naive Combinatorial Immunoglobulin Library," Proceedings of the National Academy of Sciences of the United States of America, vol. 89, Apr. 1992, pp. 3576-3580.

Davies et al., "Affinity Improvement of Single Antibody VH Domains: Residues in all Three Hypervariable Regions Affect Antigen Binding," Immunotechnology, vol. 2, May 13, 1996, pp. 169-179.
Thompson et al., "Affinity Maturation of a High-Affinity Human Monoclonal Antibody Against the Third Hypervariable Loop of Human Immunodeficiency Virus: Use of Phage Display to Improve Affinity and Broaden Strain Reactivity," Journal of Molecular Biology, vol. 256, 1996, pp. 77-88.
Boder et al., "Directed Evolution of Antibody Fragments with Monovalent Femtomolar Antigen-Binding Affinity," Proceedings of the National Academy of Sciences of the United States of America, vol. 97, No. 20, Sep. 26, 2000, pp. 10701-10705.
Furukawa et al., "A Role of the Third Complementarity-Determining Region in the Affinity Maturation of an Antibody," The Journal of Biological Chemistry, vol. 276, No. 29, Jul. 20, 2001, pp. 27622-27628.
Short et al., "Complementary Combining Site Contact Residue Mutations of the Anti-Digoxin Fab 26-10 Permit High Affinity Wild-Type Binding," The Journal of Biological Chemistry, vol. 277, No. 19, May 10, 2002, pp. 16365-16370.
Kokame et al., "FRETS-VWF73, a First Fluorogenic Substrate for ADAMTS13 Assay," British Journal of Haematology, vol. 129, 2005, pp. 93-100.
Muia et al., "An Optimized Fluorogenic ADAMTS13 Assay with Increased Sensitivity for the Investigation of Patients with Thrombotic Thrombocytopenic Purpura," Journal of Thrombosis and Haemostasis, vol. 11, 2013, pp. 1511-1518.
Vanhoorelbeke et al., "A Reliable and Reproducible ELISA Method to Measure Ristocetin Cofactor Activity of von Willebrand Factor," Thromb and Haemost, vol. 83, 2000, pp. 107-113.
Bartoli et al., "Insights into the Mechanism(s) of von Willebrand Factor Degradation During Mechanical Circulatory Support," The Journal of Thoracic and Cardiovascular Surgery, vol. 147, May 2014, pp. 1634-1643.
Crawley et al., "Unraveling the Scissile Bond: How ADAMTS13 Recognizes and Cleaves von Willebrand Factor," Blood, vol. 118, No. 12, Sep. 2011, pp. 3212-3221.
De Ceunynck et al., "Local Elongation of Endothelial Cell-Anchored von Willebrand Factor Strings Precedes ADAMTS13 Protein-Mediated Proteolysis," The Journal of Biological Chemistry, vol. 286, No. 42, Oct. 21, 2011, pp. 36361-36367.
Deforche et al., "Linker Regions and Flexibility Around the Metalloprotease Domain Account for Conformational Activation of ADAMTS-13," Journal of Thrombosis and Haemostasis, vol. 13, 2015, pp. 2063-2075.
Feys et al., "Multi-Step Binding of ADAMTS-13 to von Willebrand Factor," Journal of Thrombosis and Haemostasis, vol. 7, 2009, pp. 2088-2095.
Feys et al., "Thrombotic Thrombocytopenic Purpura Directly Linked with ADAMTS13 Inhibition in the Baboon (Papio Ursinus)," Blood, vol. 116, No. 12, Sep. 23, 2010, pp. 2005-2010.
Feys et al., "Inhibition of von Willebrand Factor-Platelet Glycoprotein Ib Interaction Prevents and Reverses Symptoms of Acute Acquired Thrombotic Thrombocytopenic Purpura in Baboons," Blood, vol. 120, No. 17, Oct. 25, 2012, pp. 3611-3614.
Rauch et al., "Antibody-Based Prevention of von Willebrand Factor Degradation Mediated by Circulatory Assist Devices," Thrombosis and Haemostatsis, vol. 112, No. 5, 2014, pp. 1014-1023.
Xiang et al., "Mechanism of von Willebrand Factor Scissile Bond Cleavage by Disintegrin and Metalloproteinase with a Thrombospondin Type 1 Motif, Member 13 (ADAMTS13)," Proceedings of the National Academy of Sciences of the United States of America, vol. 108, No. 28, Jul. 12, 2011, pp. 11602-11607.
Zanardelli et al., "A Novel Binding Site for ADAMTS13 Constitutively Exposed on the Surface of Globular VWF," Blood, vol. 114, No. 13, Sep. 24, 2009, pp. 2819-2828.
International Preliminary Report on Patentability from PCT Application No. PCT/EP2016/080229, dated Nov. 10, 2017.
International Search Report from PCT Application No. PCT/EP2016/080229, dated Mar. 14, 2017.

DNA sequence [SEQ ID NO: 1] and amino sequence [SEQ ID NO: 2] of 3H9 variable heavy chain

```
GAG GTG CAG CTG GTG GAG TCT GGG GGA GAC  30
 E   V   Q   L   V   E   S   G   G   D   10

TTA GTG AAG CCT GGA GGG TCC CTG AAA CTC  60
 L   V   K   P   G   G   S   L   K   L   20

TCC TGT GCA GCC TCT GGA TTC ACT TTC AGT  90
 S   C   A   A   S   G   F   T   F   S   30
                    ********CDR1*******
AGC TAT GGC ATG TCT TGG GTT CGC CAG ACT 120
 S   Y   G   M   S   W   V   R   Q   T   40
***********
CCA GAC AAG AGG CTG GAG TGG GTC GCA ACC 150
 P   D   K   R   L   E   W   V   A   T   50

ATT AGT AGT GGT GGA ACT TAC ACC TAC TAT 180
 I   S   S   G   G   T   Y   T   Y   Y   60
***********CDR2****************

GCA GAC ACT GTG AAG GGG CGA TTC ACC ATC 210
 A   D   T   V   K   G   R   F   T   I   70

TCC AGA GAC AAT GCC AAG AAC ACC CTG TAC 240
 S   R   D   N   A   K   N   T   L   Y   80

CTG CAA ATG AGC AGT CTG ACG TCT GAA GAC 270
 L   Q   M   S   S   L   T   S   E   D   90

TCA GCC ATG TTT TAC TGT GCA AGA CGG GTG 300
 S   A   M   F   Y   C   A   R   R   V  100
                         ***************

GCT TGG GAC TTC GGT AGT ACC TAC GAC TAT 330
 A   W   D   F   G   S   T   Y   D   Y  110
**************CDR3*********************

GCT ATG GAC TAC TGG GGC CAA GGG ACC ACG 360
 A   M   D   Y   W   G   Q   G   T   T  120
***************

GTC ACC                                  366
 V   T   *                               122

CDR1  GFTFSSYG              [SEQ ID NO: 3]
CDR2  ISSGGTYT              [SEQ ID NO: 4]
CDR3  ARRVAWDFGSTYDYAMDY    [SEQ ID NO: 5]
```

Figure 1

DNA sequence [SEQ ID NO: 6] and amino sequence [SEQ ID NO: 7] of 3H9 variable ligth chain

```
GAC ATT GAG CTC ACC CAG TCT CCA GCC ACC  30
 D   I   E   L   T   Q   S   P   A   T   10

CTG TCT GTG ACT CCA GGA GAT AGA GTC GGT  60
 L   S   V   T   P   G   D   R   V   G   20

CTT TCC TGC AGG GCC AGT CAA AGT CTT AGC  90
 L   S   C   R   A   S   Q   S   L   S   30
                         ******CDR1*****
AAC TAC CTA CAC TGG TAT CAA CAA AAA TCA 120
 N   Y   L   H   W   Y   Q   Q   K   S   40
*******
CAT GAG TCT CCA AGG CTT CTC ATC AAC TAT 150
 H   E   S   P   R   L   L   I   N   Y   50
                                     ***
GCT TCC CAG TCC ATC TCT GGG ATC CCC TCC 180
 A   S   Q   S   I   S   G   I   P   S   60
CDR2***
AGG TTC AGT GGC AGT GGA TCA GGG ACA GAT 210
 R   F   S   G   S   G   S   G   T   D   70

TTC ACT CTC AGT ATC AAC AGT GTG GAG ACT 240
 F   T   L   S   I   N   S   V   E   T   80

GAA GAT TTT GGA ATG TGT TTC TGT CAA CAG 270
 E   D   F   G   M   C   F   C   Q   Q   90
                                 *******
AGT AAC AGC TGG CCT CTC ACG TTC GGT GCT 300
 S   N   S   W   P   L   T   F   G   A   100
CDR3*********************

GGG ACC AAG CTG                          312
 G   T   K   L   *                       104

CDR1  QSLSNY     [SEQ ID NO: 8]
CDR2  YAS
CDR3  QQSNSWPLT  [SEQ ID NO:9]
```

Figure 2

DNA sequence [SEQ ID NO: 10] and amino sequence [SEQ ID NO: 11] of 17C7 variable heavy chain

```
GAG GTG CAG CTG GTG GAG TCT GGG GGA GAC  30
 E   V   Q   L   V   E   S   G   G   D   10

TTA GTG AAG TCT GGA GGG TCC CTG AAA CTC  60
 L   V   K   S   G   G   S   L   K   L   20

TCC TGT GCA GCC TCT GGA TTC ATT TTC AGT  90
 S   C   A   A   S   G   F   I   F   S   30

AAT TAT GCC ATG TCT TGG GTT CGC CAG ACT 120
 N   Y   A   M   S   W   V   R   Q   T   40
*******CDR1********

CCG GAG AAG AGG CTG GAG TGG GGC GCA ACC 150
 P   E   K   R   L   E   W   G   A   T   50
                                     ***

ATT ACT ACT GGT GGT TTT TAC ACC TTC TAT 180
 I   T   T   G   G   F   Y   T   F   Y   60
***********CDR2***********************

TCA GAC AGT GTG AAG GGT CGA TTC ACC ATC 210
 S   D   S   V   K   G   R   F   T   I   70
*********************

TCC AGA GAC AAT GCC AAG AAC ACC CTG TAC 240
 S   R   D   N   A   K   N   T   L   Y   80

CTG CAA ATG AGT AGT CTG AGG TCT GAG GAC 270
 L   Q   M   S   S   L   R   S   E   D

ACG GCC ATG TAT TAC TGT GCA AGA CAT AGG 300
 T   A   M   Y   Y   C   A   R   H   R   90
                                 *******

TAC GAC GAT TAC TAT GCT TTG GAC TAC TGG 330
 Y   D   D   Y   Y   A   L   D   Y   W  100
*****CDR3************************

GGT CAA GGA ACC TCA GTC ACC GTC TCC TCA 360
 G   Q   G   T   S   V   T   V   S   S  120

CDR1  NYAMS                [SEQ ID NO:12]
CDR2  TITTGGFYTFYSDSVKG    [SEQ ID NO:13]
CDR3  HRYDDYYALDY          [SEQ ID NO:14]
```

Figure 3

DNA sequence [SEQ ID NO: 15] and amino sequence [SEQ ID NO: 16] of 17C7 variable light chain

```
GAA AAT GTT CTC ACC CAG TCT CCA GCA ATC     30
 E   N   V   L   T   Q   S   P   A   I      10

ATG TCT ACA TCT CCA GGG GAA AAG GTC ACC     60
 M   S   T   S   P   G   E   K   V   T      20

ATG ACC TGT AAT GTC AGC TCA AGT GTA AGT     90
 M   T   C   N   V   S   S   S   V   S      30
             *************CDR1*********

TAC ATG CGC TGG TTC CAG CAG AAG TCA AGC    120
 Y   M   R   W   F   Q   Q   K   S   S      40
**********

ACC TCC CCC AAA CTA TGG ATT TAT GAC ACA    150
 T   S   P   K   L   W   I   Y   D   T      50
                                 *******
TCC AAA CTG GCT TCT GGA GTC CCA GGT CGC    180
 S   K   L   A   S   G   V   P   G   R      60
CDR2***************

TTC AGT GGC AGT GGG TCT GGA CAC TCT TAC    210
 F   S   G   S   G   S   G   H   S   Y      70

TCT CTC ACG ATC AGT AGC ATG GAG GCT GAC    240
 S   L   T   I   S   S   M   E   A   D      80

GAT GTT GCC ACT TAT TAC TGT TTT CAG GGG    270
 D   V   A   T   Y   Y   C   F   Q   G      90
                             ***********

AAT GGG TAC CCA CTC ACG TTC GGT GCT GGG    300
 N   G   Y   P   L   T   F   G   A   G     100
CDR3******************

ACC AAG CTG GAG CTG AAA                    318
 T   K   L   E   L   K                      106

CDR1  NVSSSVSYMR   [SEQ ID NO:17]
CDR2  DTSKLAS      [SEQ ID NO:18]
CDR3  FQGNGYPLT    [SEQ ID NO:19]
```

Figure 4

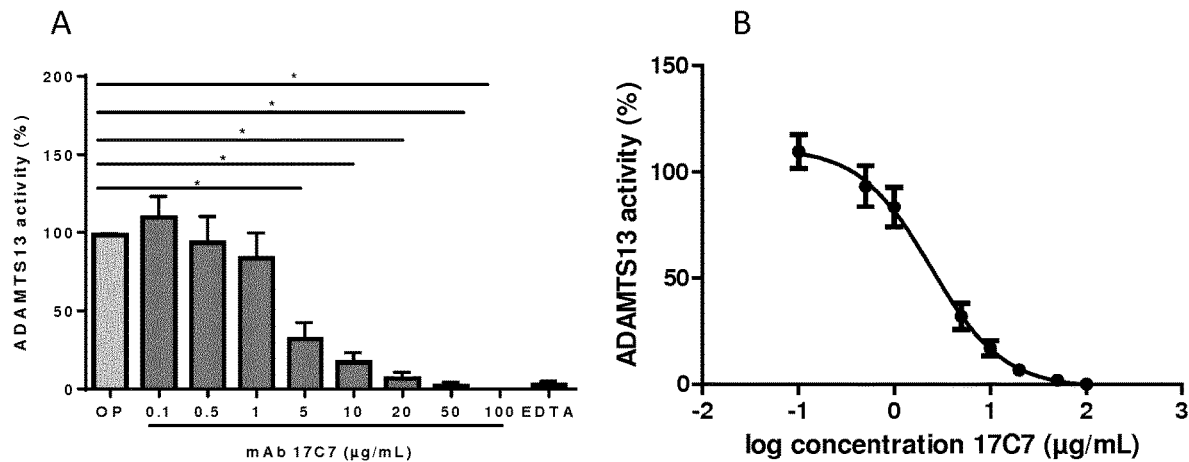
Figure 14
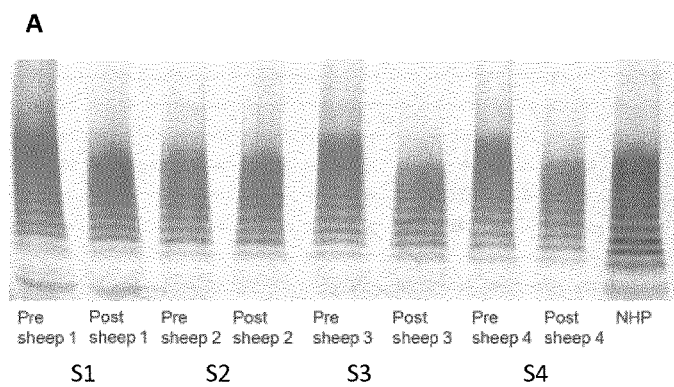
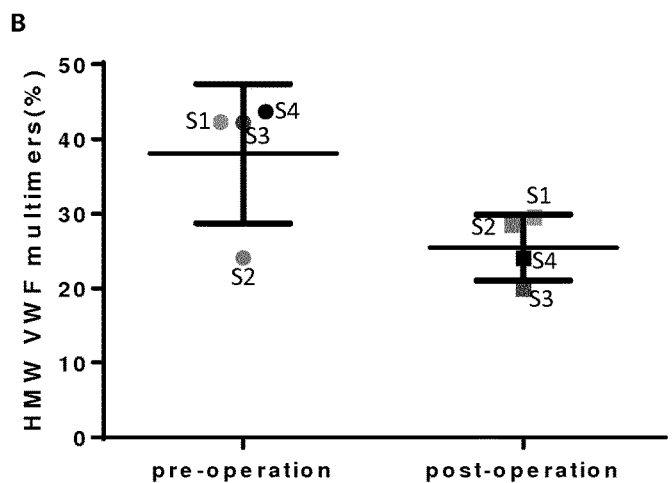
Figure 15

HAEMORRHAGIC DISORDER DUE TO VENTRICULAR ASSIST DEVICE

The deposit of micro-organisms has been deposited and accepted under the Budapest Treaty. All restrictions imposed by the depositor on the availability to the public of the deposited material will be irrevocably removed upon the granting of the patent.

FIELD OF THE INVENTION

The present invention relates to treatments of haemorrhagic complications such as bleeding disorders due to a circulatory assist device implant.

The present invention further relates to molecules such as monoclonal antibodies which selectively bind to ADAMTS13 and inhibit its enzymatic activity.

BACKGROUND OF THE INVENTION

Human ADAMTS13 (A Disintegrin And Metalloproteinase with a ThromboSpondin type 1 motif, member 13), is a zinc-containing metalloprotease enzyme that cleaves von human von Willebrand factor (VWF).

An anti-ADAMTS13 monoclonal antibody 3H9 has been described [Feys et al (2010) *Blood* 116, 2005-2010]. mAb 3H9 binds an epitope in the metalloprotease domain of ADAMTS13, and has been shown to inhibit the human ADAMTS13 and to cross-inhibit ADAMTS13 in baboon plasma. The antibody induced thrombotic thrombocytopenic purpura (TTP) in baboons at two boluses of 600 µg/kg administered intravenously to baboons at 0 h and 48 h, showing that ADAMTS13 function is essential for maintaining microvascular integrity in nonhuman primates. The anti-ADAMTS13 monoclonal antibody 3H9 has also been shown to inhibit the ADAMTS13 mediated proteolysis of VWF strings, which are UL-VWF multimers decorated with platelets persisting on the endothelial surface both in vitro and in vivo for several minutes (De Ceunynck et al (2011) *J Biol Chem* 286: 36361-36367), as well as the ADAMTS13 mediated proteolysis of the VWF peptide VWF73 (Deforche et al (2015) *J Thromb Haemost.* 13(11), 2063-2075).

In the above studies, ADAMTS13 inhibition has been studied in its relation to thrombotic thrombocytopenic purpura. Linking ADAMTS13 inhibition using 3H9 with treatment of aVWS was not reported.

Continuous-flow left ventricular assist devices (CF-LVADs) have become the standard of care for patients with end-stage heart failure (HF). However, haemorrhagic episodes in patients carrying implanted circulatory assist devices represent a severe life-threatening clinical complication, which is currently the leading complication in patients undergoing left ventricular assist device (LVAD) support. Such bleeding complications are a major source of morbidity and reoperation after left ventricular assist device (LVAD) implantation, yet remain poorly characterized in patients receiving LVADs (Schaffer J M (2011) *Ann Thorac Surg.* 91, 740-747, 747-749).

Rauch et al. (2014) *Thromb Haemost.* 112(5), 1014-1023 disclose the partial inhibition of VWF-ADAMTS13 interactions using an anti-VWF antibody to prevent VWF degradation mediated by circulatory assist devices.

Alternative strategies targeting the other partner in the VWF-ADAMTS13 have not been investigated.

There is thus a need in the art for an efficient treatment for this disorder.

SUMMARY OF THE INVENTION

One aspect of the invention relates to antigen binding molecules specifically binding to ADAMTS13 and inhibiting VWF cleavage by ADAMTS13 for use in the treatment or prevention of a haemorrhagic complication or bleeding disorder in a subject carrying an implanted circulatory assist device.

Further, the methods and compounds of the present invention can be used to treat or prevent haemorrhagic complications or bleeding disorders caused by high shear stress in patients without implanted LVAD like patients suffering from Heyde's syndrome and patients with a veno-venous Extra Corporeal Membrane Oxygenation support (ECMO) for respiratory support.

The antigen binding molecule can be an antibody, an antibody-like scaffold or an antibody fragment.

The antibody can be a specific polyclonal antibody, a monoclonal antibody, a full-length antibody, a binding fragment of an antibody and a surrogate of an antibody.

The antigen binding molecule can be aFab', F(ab')2, Fab, Fv, vIgG, scFv fragments and surrobodies, rIgG, disulfide-stabilized Fv antibodies (dsFv), diabodies, triabodies, and single domain antibodies, such as a camelized antibody or nanobody or humanized camel or shark antibody or nanobody.

A specific embodiment of the antigen binding molecule is a fragment of a monoclonal antibody of the group consisting of a scFV, Fab, Fab2, F(ab')2, Fv or dAb.

A specific embodiment of the antigen binding molecule is a chimeric or humanized antibody or antigen-binding fragment thereof.

A specific embodiment of the antigen binding molecule is an antibody or antibody fragment comprising:
a variable heavy chain wherein the sequence of the CDR1, CDR2 and CDR3 region correspond to respectively, the sequence of SEQ ID NO: 12, SEQ ID NO:13, and SEQ ID NO:14 and comprising
a variable light chain wherein the sequence of the CDR1, CDR2 and CDR3 region correspond to respectively, the sequence of SEQ ID NO: 17, SEQ ID NO:18, and SEQ ID NO:19.

A specific embodiment of the antigen binding molecule is an antibody or antibody fragment wherein the variable domain comprises a VH region that has outside the CDR regions at least 80% identity with the amino acid sequence of SEQ ID NO: 11 and a VL region that has outside the CDR regions at least 80% identity to the amino acid sequence of SEQ ID NO: 16.

A specific embodiment of the antigen binding molecule is an antibody or antibody fragment comprising
a variable heavy chain wherein the sequence of the CDR1, CDR2 and CDR3 region correspond to respectively, the sequence of SEQ ID NO: 3, SEQ ID NO:4, and SEQ ID NO:5 and comprising
a variable light chain wherein the sequence of the CDR1, CDR2 and CDR3 region correspond to respectively, the sequence of SEQ ID NO: 8, the sequence YAS, and SEQ ID NO:9.

A specific embodiment of the antigen binding molecule is an antibody or antibody fragment wherein the variable domain comprises a VH region that has outside the CDR regions at least 80% identity with the amino acid sequence of SEQ ID NO: 2 and a VL region that has outside the CDR regions at least 80% identity to the amino acid sequence of SEQ ID NO: 7.

A specific embodiment of the antigen binding molecule is an antibody or antibody fragment of a humanized antibody of the antibody produced by a hybridoma deposited under the Budapest Treaty at the Belgian Coordinated Collections of Microorganisms BCCM™/LMBP Collection under No. LMBP 11316CB.

A specific embodiment of the antigen binding molecule is a humanized antibody comprising CDRs of the antibody produced by a hybridoma deposited under the Budapest Treaty at the Belgian Coordinated Collections of Microorganisms BCCM™/LMBP Collection under No. LMBP 11316CB.

In specific embodiments the antigen binding molecules bind to ADAMTS13 with a dissociation constant (KD) of 150 pM or less, as determined by real-time biospecific interaction analysis (BIA) using surface plasmon resonance (SPR) technology, or with an IC50 of 100 pM or less.

In specific embodiments the antigen binding molecules bind to a neutralizing epitope of human ADAMTS13 with an affinity of at least about $5 \times 10^4$ liter/mole as measured by an association constant (Ka).

The above cited antigen binding molecules can be used in individuals whereby the circulatory assist device implanted is a ventricular assist device (VAD), or more specifically a left ventricular assist device (LVAD).

Another aspect of the invention relates to antigen binding molecules specifically binding to ADAMTS13 and inhibiting ADAMTS13 which are antibodies or antibody fragments comprising: a variable heavy chain wherein the sequence of the CDR1, CDR2 and CDR3 region correspond to respectively, the sequence of SEQ ID NO: 12, SEQ ID NO:13, and SEQ ID NO: 14, and comprising a variable light chain wherein the sequence of the CDR1, CDR2 and CDR3 region correspond to respectively, the sequence of SEQ ID NO: 17, SEQ ID NO:18, and SEQ ID NO:19.

In specific embodiments the variable domain comprises a VH region that has outside the CDR regions at least 80%, at least 90%, or at least 95% identity to amino acid sequence SEQ ID NO:11 and comprises a VL region comprising an amino acid sequence which has outside the CDR regions at least 80%, at least 90%, or at least 95% identity to amino acid sequence SEQ ID NO: 16.

Another aspect of the invention relates to antigen binding molecules specifically binding to ADAMTS13 and inhibiting ADAMTS13 which are antibodies or antibody fragments comprising: a variable heavy chain wherein the sequence of the CDR1, CDR2 and CDR3 region correspond to respectively, the sequence of SEQ ID NO: 3, SEQ ID NO:4, and SEQ ID NO: 5, and comprising a variable light chain wherein the sequence of the CDR1, CDR2 and CDR3 region correspond to respectively, the sequence of SEQ ID NO: 8, the sequence YAS, and SEQ ID NO: 9.

In specific embodiments the variable domain comprises a VH region that has outside the CDR regions at least 80%, at least 90%, or at least 95% identity to amino acid sequence SEQ ID NO: 2 and VL region comprising an amino acid sequence which has outside the CDR regions at least 80% at least 90%, or at least 95% identity to amino acid sequence SEQ ID NO: 7.

Another aspect of the present invention relates to methods of treating or preventing a haemorrhagic complication or bleeding disorder in a subject carrying an implanted circulatory assist device comprising the step of administering to said individual an antigen binding molecule specifically binding to ADAMTS13 and inhibiting VWF cleavage by ADAMTS13.

In specific embodiments the antigen binding molecule specifically binding to ADAMTS13 is an antibody or antibody fragment comprising:
a variable heavy chain wherein the sequence of the CDR1, CDR2 and CDR3 region correspond to respectively, the sequence of SEQ ID NO: 12, SEQ ID NO:13, and SEQ ID NO: 14, and comprising
a variable light chain wherein the sequence of the CDR1, CDR2 and CDR3 region correspond to respectively, the sequence of SEQ ID NO: 17, SEQ ID NO:18, and SEQ ID NO:19.

In specific embodiments the antigen binding molecule specifically binding to ADAMTS13 has a variable domain comprising a VH region that has outside the CDR regions at least 80% identity to amino acid sequence SEQ ID NO:11 and comprising a VL region comprising an amino acid sequence which has outside the CDR regions at least 80% identity to amino acid sequence SEQ ID NO: 16.

In specific embodiments the said antigen binding molecule specifically binding to ADAMTS13 is an antibody or antibody fragment comprising:
a variable heavy chain wherein the sequence of the CDR1, CDR2 and CDR3 region correspond to respectively, the sequence of SEQ ID NO: 3, SEQ ID NO:4, and SEQ ID NO: 5, and comprising
a variable light chain wherein the sequence of the CDR1, CDR2 and CDR3 region correspond to respectively, the sequence of SEQ ID NO: 8, the sequence YAS, and SEQ ID NO: 9.

In specific embodiments the antigen binding molecule specifically binding to ADAMTS13 has a variable domain comprising a VH region that has outside the CDR regions at least 80% identity to amino acid sequence SEQ ID NO:2 and comprising a VL region comprising an amino acid sequence which has outside the CDR regions at least 80% identity to amino acid sequence SEQ ID NO: 7.

The present invention further relates to the use of an antibody, as defined in the second or fourth aspect, in a sheep animal model with an implanted LVAD device.

The present invention provides monoclonal antibodies (mAb) directed against ADAMTS13 and the use of these monoclonal anti-ADAMTS13 antibodies in the prevention or treatment of bleeding in cardiac patients carrying an implanted LVAD device.

These mAbs bind an epitope in the metalloprotease domain containing the active site of human ADAMTS13 or in other ADAMTS13 domains containing exosites important for binding to VWF. These antibodies inhibit the human ADAMTS13 function.

The 3H9 antibody also cross-inhibits ADAMTS13 in baboon, dog, cynomolgus (*Macaca fascicularis*) and porcine plasma.

The 17C7 antibody shows cross-inhibition ADAMTS13 with baboon, cynomolgus (*Macaca fascicularis*) and sheep plasma.

The present invention accordingly provides methods and uses wherein murine or humanised antibodies are used in non-human, non-mouse model organisms with an LVAD such as baboons, cynomolgus monkeys, dogs, pigs or sheep to study the effect of ADAMTS13 inhibition on restoration of high molecular weight VWF multimers.

Absence of high molecular weight VWF multimers, as observed in LVAD patients, leads to the bleeding disorder acquired von Willebrand syndrome (aVWS).

These methods and uses are non-therapeutic uses and are typically followed by sacrificing the animal.

These anti-ADAMTS13 Mabs also inhibit ADAMTS13 mediated proteolysis of von Willebrand factor (VWF) strings, which are UL-VWF multimers decorated with platelets persisting on the endothelial surface both in vitro and in vivo for several minutes as well as the ADAMTS13 mediated proteolysis of the von Willebrand factor peptide VWF73.

The protease ADAMTS13 has VWF as sole substrate. The methods and compounds of the present invention specifically prevent the ADAMTS13 mediated processing of VWF whereby the other functions of VWF remain preserved. This has several advantages compared to VWF inhibition:

VWF has other important functions besides being a substrate for ADAMTS13. VWF is a major player in primary haemostasis. It binds via its A3 domain to collagen present in the damaged vessel wall and via its A1 domain to platelets. As the A2 domain is situated between the A1 and A3 domain, antibodies binding to the A2 domain can interfere with the haemostatic function of VWF.

The current available anti-VWF antibody only partially inhibits the binding of VWF to ADAMTS13, hence this antibody might not be potent enough to fully restore high molecular weight VWF multimers in vivo.

VWF consists of a series of multimers with sizes of up to 20 million Dalton. The binding of antibodies to VWF would even further increase the size of these VWF multimers, leading to enhanced clearance of VWF.

The present invention relates to methods of treatment by human ADAMTS13 inhibition, in a subject in need thereof, of haemorrhagic complications such as bleeding disorders due to a circulatory assist device implant. In particular it concerns to treat or prevent bleeding after left ventricular assist device (LVAD) implantation in heart patients by a selective inhibition of human ADAMTS13. The invention also provides antibodies, compositions and methods for preventing and/or treating such bleeding disorders in a subject carrying an implanted circulatory assist device or for preventing and/or treating such bleeding disorders caused by an implanted circulatory assist device using said antibodies, compositions or methods.

More particularly the present invention relates to methods for treating heart patients carrying an implanted circulatory assist device, for instance a left ventricular assist device (LVAD), by an isolated antigen binding protein comprising at least one first immunoglobulin variable domain capable of binding to human ADAMTS13 to prevent or treat bleeding or haemorrhagic disorders induced by or due to the ventricular assist device implantation.

The present invention also relates to an antibody, or functional fragments thereof, against human ADAMTS13 protein suitable for the purposes of the present invention and it provides furthermore a combination of such antibodies, or functional fragments thereof, nucleic acids encoding such antibodies and antibody fragments, cell lines producing such antibodies and antibody fragments, and antibody compositions against human ADAMTS13.

The present invention provides a monoclonal antibody AB11313CB (3H9) shown in FIGS. 1 and 2, with CDRs SEQ ID NO: 3, SEQ ID NO: 4, SEQ ID NO: 5, and SEQ ID NO: 8, the tripeptide YAS and SEQ ID NO: 9 or comprising the amino acid sequences of SEQ ID NO:2 and SEQ ID NO:7, directed against ADAMTS13 and the use of this monoclonal (mAb) anti-ADAMTS13 antibody in the prevention or treatment of bleeding disorders in cardiac patients carrying an implanted circulatory assist device, such as an LVAD device.

The present invention further provides a monoclonal antibody 17C7, with CDRs shown in FIGS. 3 and 4, with CDRs SEQ ID NO: 12, SEQ ID NO: 13, SEQ ID NO: 14, and SEQ ID NO: 17, SEQ ID NO: 18 and SEQ ID NO: 19, or comprising the amino acid sequences of SEQ ID NO:11 and SEQ ID NO:16, directed against ADAMTS13 and the use of this monoclonal (mAb) anti-ADAMTS13 antibody in the prevention or treatment of bleeding disorders in cardiac patients carrying an implanted circulatory assist device, such as an LVAD device.

Some embodiments of the invention are set forth in claim format directly below:

1. A molecule that is an antibody, antibody-like scaffold or antibody fragment that binds ADAMTS13 for use in the treatment or prevention of a haemorrhagic complication or bleeding disorder in a subject carrying an implanted circulatory assist device.

2. A molecule that is an antigen binding protein comprising at least one first immunoglobulin variable domain capable of binding to human ADAMTS13 for use in the treatment or prevention of a haemorrhagic complication or bleeding disorder in a subject carrying an implanted circulatory assist device.

3. Molecule according to any one of the formats 1 to 2, whereby the ADAMTS13 binding molecule is an ADAMTS13 inhibitor.

4. Molecule according to any one of the formats 1 to 3, whereby the ADAMTS13 binding or inhibiting molecule is selected from the group consisting of a specific polyclonal antibody, a monoclonal antibody, a full-length antibody, a binding fragment of an antibody and a surrogate of an antibody.

5. Molecule according to any one of the formats 1 to 3, whereby the ADAMTS13 binding or inhibiting molecule is selected from the group consisting of a Fab', F(ab')2, Fab, Fv, vIgG, scFv fragments and surrobodies, rIgG, disulfide-stabilized Fv antibodies (dsFv), diabodies, triabodies, and single domain antibodies, such as a camelized antibody or nanobody or humanized camel or shark antibody or nanobody and capable of binding to human ADAMTS13.

6. Molecule according to any one of the formats 1 to 3, whereby the ADAMTS13 binding or inhibiting molecule is an ADAMTS13 antigen-binding fragment of a monoclonal antibody of the group consisting of a scFV, Fab, Fab2, F(ab')2, Fv or dAb and capable of binding to human ADAMTS13.

7. Molecule according to any one of the formats 1 to 6, whereby the ADAMTS13 binding or inhibiting molecule is a chimeric or humanized antibody or antigen-binding fragment thereof and capable of binding to human ADAMTS13.

8. Molecule according to any one of the formats 1 to 7, whereby the ADAMTS13 binding or inhibiting molecule specifically binds to ADAMTS13, in part.

9. Molecule according to any one of the formats 1 to 8, whereby the ADAMTS13 binding or inhibiting molecule specifically binds to human ADAMTS13.

10. Molecule according to any one of the formats 1 to 9, whereby the ADAMTS13 binding or inhibiting molecule is a monoclonal antibody comprising at least one heavy chain variable domain having an amino acid sequence which has at least 80% identity to amino acid sequence SEQ ID NO: 2 and at least one light chain variable domain having an amino acid sequence which has at least 80% identity to amino acid sequence SEQ ID NO: 7.

11. Molecule according to any one of the formats 1 to 9, whereby the ADAMTS13 binding or inhibiting molecule is a monoclonal antibody comprising at least one heavy chain variable domain having an amino acid sequence which has at least 90% identity to amino acid sequence SEQ ID NO: 2 and at least one light chain variable domain having an amino acid sequence which has at least 90% identity to amino acid sequence SEQ ID NO: 7.

12. Molecule according to any one of the formats 1 to 9, whereby the ADAMTS13 binding or inhibiting molecule is a monoclonal antibody comprising at least one heavy chain variable domain having an amino acid sequence which has at least 95% identity to amino acid sequence SEQ ID NO: 2 and at least one light chain variable domain having an amino acid sequence which has at least 95% identity to amino acid sequence SEQ ID NO: 7.

13. Molecule according to any one of the formats 1 to 9, wherein the ADAMTS13 binding or inhibiting molecule is an antibody or antibody fragment comprising a heavy chain CDR comprising the amino acid sequence of SEQ ID NO: 3.

14. Molecule according to any one of the formats 1 to 9, wherein the ADAMTS13 binding or inhibiting molecule is an antibody or antibody fragment comprising a heavy chain CDR comprising the amino acid sequence of SEQ ID NO: 4.

15. Molecule according to any one of the formats 1 to 9, wherein the ADAMTS13 binding or inhibiting molecule is an antibody or antibody fragment comprising a heavy chain CDR comprising the amino acid sequence of SEQ ID NO: 5.

16. Molecule according to any one of the formats 1 to 9, wherein the ADAMTS13 binding or inhibiting molecule is an antibody or antibody fragment comprising a light chain CDR comprising the amino acid sequence of SEQ ID NO: 8.

17. Molecule according to any one of the formats 1 to 9, wherein the ADAMTS13 binding or inhibiting molecule is an antibody or antibody fragment comprising a light chain CDR comprising the amino acid sequence YAS.

18. Molecule according to any one of the formats 1 to 9, wherein the ADAMTS13 binding or inhibiting molecule is an antibody or antibody fragment comprising a light chain CDR comprising the amino acid sequence of SEQ ID NO: 9.

19. Molecule according to any one of the formats 1 to 9, whereby the ADAMTS13 binding or inhibiting molecule is a monoclonal antibody comprising a heavy chain comprising CDRH1, CDRH2 and CDRH3 and a light chain comprising CDRL1, CDRL2 and CDRL3, wherein the CDRs of the heavy chain are selected from the group of: a) CDRH1 having at least about 80% sequence identity to amino acid sequence GFTFSSYG (SEQ ID NO: 3); b) CDRH2 having at least about 80% sequence identity to amino acid sequence ISSGGTYT (SEQ ID NO: 4); and c) CDRH3 having at least about 80% sequence identity to amino acid sequence AARVAWDFGSTYDYAMDY (SEQ ID NO: 5); and the CDRs of the light chain are selected from the group of: d) CDRL1 having at least about 80% sequence identity to amino acid sequence QSLSNY (SEQ ID NO:8); e) CDRL2 having at least about 80% sequence identity to amino acid sequence YAS and f) CDRL3 having at least about 80% sequence identity to amino acid sequence QQSNSWPLT (SEQ ID NO:9).

20. Molecule according to any one of the formats 1 to 9, whereby the molecule is a monoclonal antibody comprising a heavy chain comprising CDRH1, CDRH2 and CDRH3 and a light chain comprising CDRL1, CDRL2 and CDRL3, wherein the CDRs of the heavy chain are selected from the group of: a) CDRH1 having at least about 90% sequence identity to amino acid sequence GFTFSSYG (SEQ ID NO: 3); b) CDRH2 having at least about 90% sequence identity to amino acid sequence ISSGGTYT (SEQ ID NO: 4); and c) CDRH3 having at least about 90% sequence identity to amino acid sequence AARVAWDFGSTYDYAMDY (SEQ ID NO: 5); and the CDRs of the light chain are selected from the group of: d) CDRL1 having at least about 90% sequence identity to amino acid sequence QSLSNY (SEQ ID NO:8); e) CDRL2 having at least about 90% sequence identity to amino acid sequence YAS; and f) CDRL3 having at least about 90% sequence identity to amino acid sequence QQSNSWPLT (SEQ ID NO:9).

21. Molecule according to any one of the formats 1 to 9, whereby the ADAMTS13 binding or inhibiting molecule is a monoclonal antibody comprising a heavy chain comprising CDRH1, CDRH2 and CDRH3 and a light chain comprising CDRL1, CDRL2 and CDRL3, wherein the CDRs of the heavy chain are selected from the group of: a) CDRH1 having at least about 95% sequence identity to amino acid sequence GFTFSSYG (SEQ ID NO: 3); b) CDRH2 having at least about 95% sequence identity to amino acid sequence ISSGGTYT (SEQ ID NO: 4); and c) CDRH3 having at least about 95% sequence identity to amino acid sequence AARVAWDFGSTYDYAMDY (SEQ ID NO: 5); and the CDRs of the light chain are selected from the group of: d) CDRL1 having at least about 95% sequence identity to amino acid sequence QSLSNY (SEQ ID NO:8); e) CDRL2 having at least about 95% sequence identity to amino acid sequence YAS; and f) CDRL3 having at least about 95% sequence identity to amino acid sequence QQSNSWPLT (SEQ ID NO:9).

22. Molecule according to any one of the formats 1 to 9, whereby the molecule is a monoclonal antibody comprising six CDRs wherein CDRH1 is GFTFSSYG (SEQ ID NO: 3), CDRH2 is ISSGGTYT (SEQ ID NO: 4), and CDRH3 is AARVAWDFGSTYDYAMDY (SEQ ID NO: 5) and CDRL1 is QSLSNY (SEQ ID NO:8), CDRL2 is YAS and CDRL3 is QQSNSWPLT (SEQ ID NO:9).

23. Molecule according to any one of the formats 1 to 9, whereby the molecule is a humanized antibody of the antibody produced by a hybridoma deposited under the Budapest Treaty at the Belgian Coordinated Collections of Microorganisms BCCM™/LMBP Collection under No. LMBP 11316CB.

24. Molecule according to any one of the formats 1 to 9, whereby the molecule is a humanized antibody comprising CDRs of the antibody produced by a hybridoma deposited under the Budapest Treaty at the Belgian Coordinated Collections of Microorganisms BCCM™/LMBP Collection under No. LMBP 11316CB.

25. Molecule according to any one of the formats 1 to 24, whereby the ADAMTS13 binding molecule comprises an antibody, or antigen-binding fragment thereof, that binds to ADAMTS13 with a dissociation constant (K D) of 150 pM or less, as determined by real-time biospecific interaction analysis (BIA) using surface plasmon resonance (SPR) technology, or with an IC50 of 100 pM or less.

26. Molecule according to any one of the formats 1 to 24, whereby the ADAMTS13 binding molecule comprises an antibody, or antigen binding fragment thereof, that binds to a neutralizing epitope of human ADAMTS13 with an affinity of at least about 5×10⁴ liter/mole as measured by an association constant (Ka).

27. Molecule according to any one of the formats 1 to 26, whereby the ADAMTS13 inhibitor further comprises a component selected from the group consisting of pharmaceutically acceptable carriers, diluents and excipients.

28. Molecule according to any one of the formats 1 to 27, whereby said circulatory assist device implanted in said subject is a ventricular assist device (VAD).

29. Molecule according to any one of the formats 1 to 27, whereby said circulatory assist device implanted in said subject is a left ventricular assist device (LVAD).

30. An isolated ADAMTS13 antibody, antibody-like scaffold or antibody fragment, characterized in that:
it comprises at least one heavy chain variable domain having an amino acid sequence which has at least 80% or 90% or 95% identity to amino acid sequence SEQ ID NO: 2 and at least one light chain variable domain having an amino acid sequence which has at least 80% or 90% or 95% identity to amino acid sequence SEQ ID NO: 7; or
it comprises at least one heavy chain variable region comprising in a CDR1 region an amino acid sequence which has at least 80% or 90% or 95% identity to SEQ ID NO: 3, in a CDR2 region an amino acid sequence which has at least 80% or 90% or 95% identity to SEQ ID NO: 4 and in a CDR3 region an amino acid sequence which has at least 80% or 90% or 95% identity to SEQ ID NO: 5; and further comprises a light chain variable region comprising in a CDR1 region an amino acid sequence which has at least 80% or 90% or 95% identity to SEQ ID NO: 8, in a CDR2 region an amino acid sequence which has at least 80% or 90% or 95% identity to the tripeptide YAS and in a CDR:3 region an amino acid sequence which has at least 80% or 90% or 95% identity to SEQ ID NO: 9.

31. The isolated ADAMTS13 antibody, antibody-like scaffold or antibody fragment according to format 30, comprising at least one heavy chain variable domain comprising an amino acid sequence as set out in SEQ ID NO: 2 and at least one light chain variable domain comprising an amino acid sequence as set out in SEQ ID NO: 7.

32. The isolated ADAMTS13 antibody, antibody-like scaffold or antibody fragment according to format 30, wherein the heavy chain variable region comprises in a CDR1 region an amino acid sequence as set out in SEQ ID NO: 3, in a CDR2 region an amino acid sequence as set out in SEQ ID NO: 4 and in a CDR3 region an amino acid sequence as set out in SEQ ID NO: 5; and wherein the light chain variable region comprises in a CDR1 region an amino acid sequence as set out in SEQ ID NO: 8, in a CDR2 with the sequence YAS and in a CDR:3 region an amino acid sequence as set out in SEQ ID NO: 9.

33. The isolated ADAMTS13 antibody, antibody-like scaffold or antibody fragment according to any one of the formats 30 to 32, which: is a monoclonal antibody; or is a mouse monoclonal IgG1 subtype; or is a humanized antibody or fragment thereof for instance a single-chain antibody, Fv fragment, a Fab fragment (e.g. Fab' fragment or a F(ab')2 fragment) or a single domain antibody; or is a human antibody or fragment thereof.

34. The antibody or antibody fragment according to any one of formats 30 to 33, further characterized in that it is secreted by the hybridoma cell line LRD-915092 deposited under the Budapest Treaty at the Belgian Coordinated Collections of Microorganisms BCCM™/LMBP Collection under No. LMBP 11316CB.

35. The antibody according to any one of formats 30 to 33, whereby the antibody is a humanized antibody of the antibody produced by a hybridoma deposited under the Budapest Treaty at the Belgian Coordinated Collections of Microorganisms BCCM™/LMBP Collection under No. LMBP 11316CB.

36. The antibody according to any one of formats 30 to 33, whereby the antibody is a humanized antibody comprising the CDRs of the antibody produced by a hybridoma deposited under the Budapest Treaty at the Belgian Coordinated Collections of Microorganisms BCCM™/LMBP Collection under No. LMBP 11316CB.

37. The isolated ADAMTS13 antibody, antibody-like scaffold or antibody fragment according to any one of formats 30 to 36, for use in the treatment or prevention of a haemorrhagic complication or bleeding disorder in a subject carrying an implanted circulatory assist device, comprising administering said antibody, antibody-like scaffold or antibody fragment to said subject.

38. An isolated nucleic acid comprising a polynucleotide encoding the antibody, antibody-like fragments or antibody fragment according to any one of the formats 30 to 37, further characterized in that it comprises the sequences SEQ ID NO: 1 and SEQ ID NO: 6.

39. An isolated cell line producing the antibody or antibody fragment according to any one of the formats 30 to 37, further characterized in that cell line is the hybridoma cell line LRD-915092 is deposited under the Budapest Treaty at the Belgian Coordinated Collections of Microorganisms BCCM™/LMBP Collection under No. LMBP 11316CB.

40. A pharmaceutical composition comprising the antibody, antibody-like fragment or antibody fragment according to any one of the formats 30 to 37, for use in the prevention or treatment of a haemorrhagic complication or bleeding disorder in a subject carrying an implanted circulatory assist device.

DETAILED DESCRIPTION OF THE INVENTION

Legends to Figures

[in the figures the Ab 3H9, (deposited as LMBP 11316CB) is also referred to as Ab11316CB]

FIG. 1 shows the nucleotide sequence, amino acid sequence and CDR regions of the variable heavy chain of the monoclonal antibody 3H9 (Ab11316CB).

FIG. 2 shows the nucleotide sequence, amino acid sequence and CDR regions of the variable light chain of the monoclonal antibody 3H9 (Ab11316CB).

FIG. 3 shows the nucleotide sequence, amino acid sequence and CDR regions of the variable heavy chain of the monoclonal antibody 17C7.

FIG. 4 shows the nucleotide sequence, amino acid sequence and CDR regions of the variable light chain of the monoclonal antibody 17C7.

Figure 5:
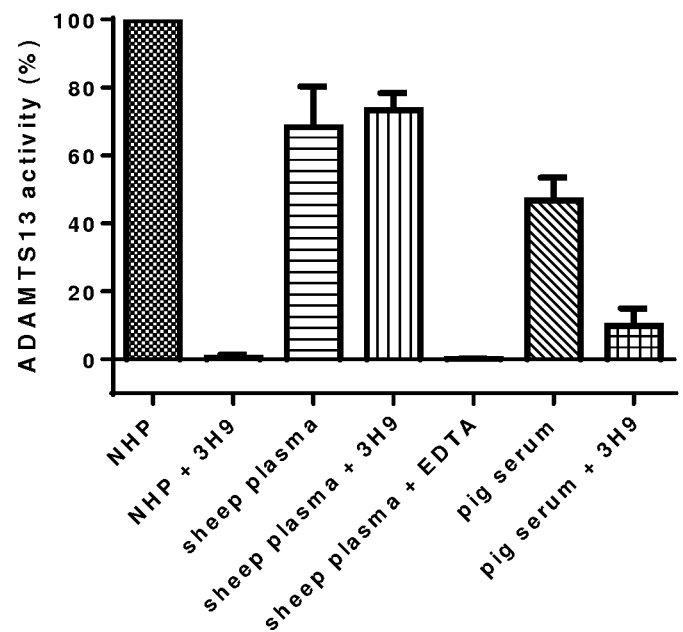

FIG. 5 demonstrates the ADAMTS13 activity in different sera/plasma samples determined through a FRETS-VWF73 assay. The activity of ADAMTS13 in human plasma (NHP) was set at 100%.

Figure 6:
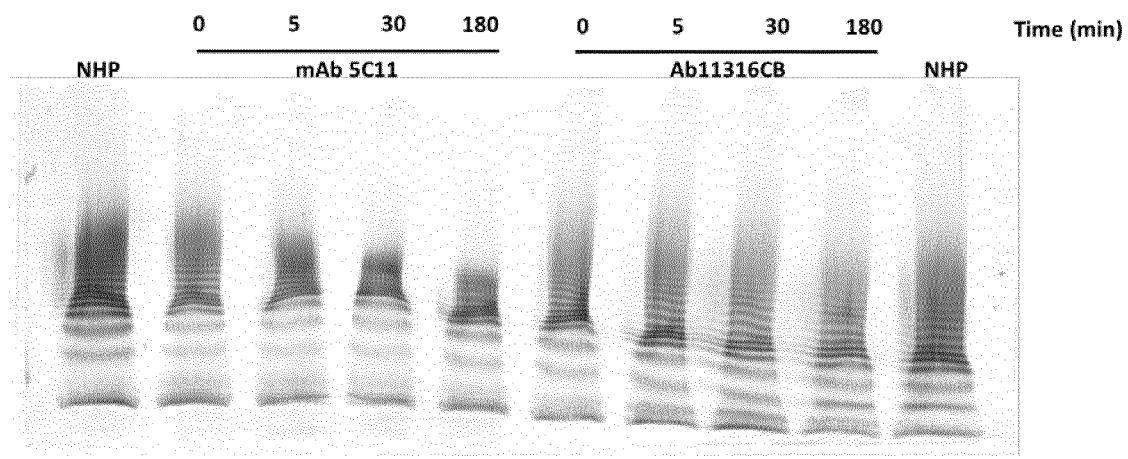

FIG. 6 provides an example of a multimer agarose gel of plasma samples in which 20 µg/ml Ab11316CB antibody was added. 1. Normal human plasma; 2. 5C11 TO; 3. 5C11 T5; 4. 5C11 T30; 5. 5C11 T180; 6. Ab11316CB TO; 7. Ab11316CB T5; 8. Ab11316CB T30; 9. Ab11316CB T180; 10. Normal human plasma.

FIGS. 7A to 7C demonstrate that blocking ADAMTS13 activity protects against loss of HMW VWF in an in vitro LVAD system. HMW VWF multimer distribution during in vitro LVAD after adding 1 µg/ml (A), 4 µg/ml (B) or 20 µg/ml (C) of the anti-ADAMTS13 antibody 5C11 or Ab11316CB.

Figure 8:
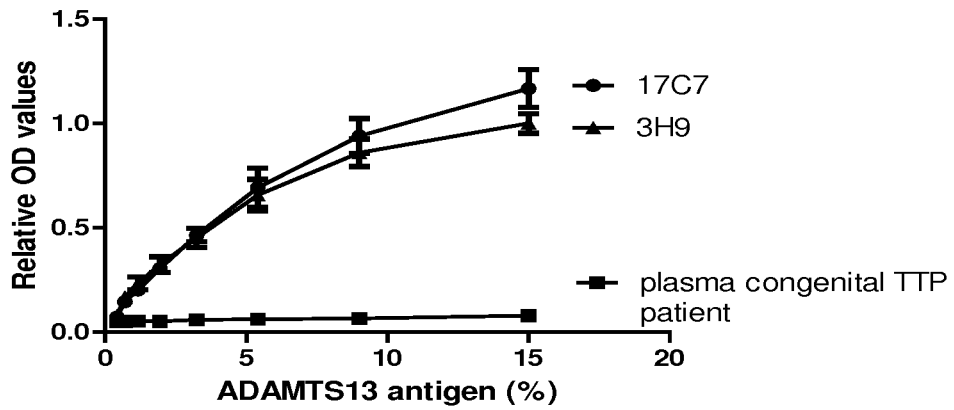

FIG. 8 shows that 17C7 and 3H9 (Ab11316CB) antibodies specifically detect ADAMTS13 in human plasma.

Figure 9:
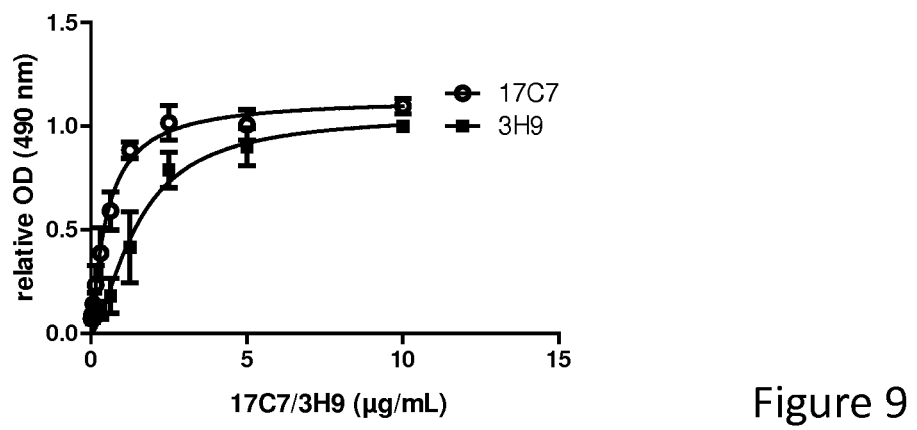

FIG. 9 shows the difference of affinity of ADAMTS13 for the 17C7 and 3H9 (Ab11316CB) antibody in capturing ADAMTS13 from plasma.

Figure 10:
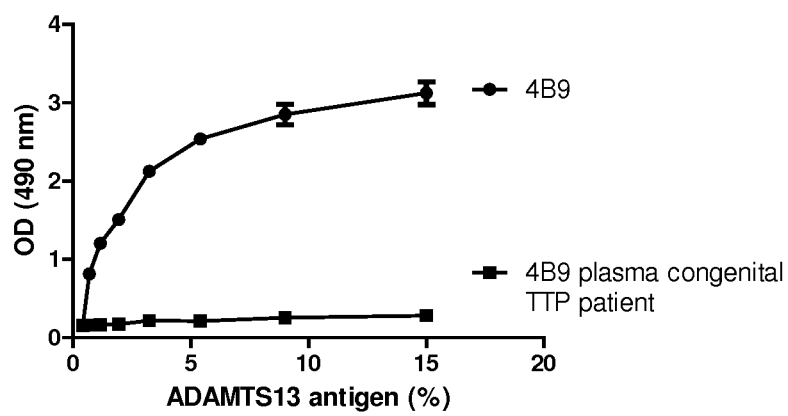

FIG. 10 shows that 17C7 can also detect ADAMTS13 in plasma, when ADAMTS13 is captured by the other anti-ADAMTS13 antibody 4B9.

Figure 11:
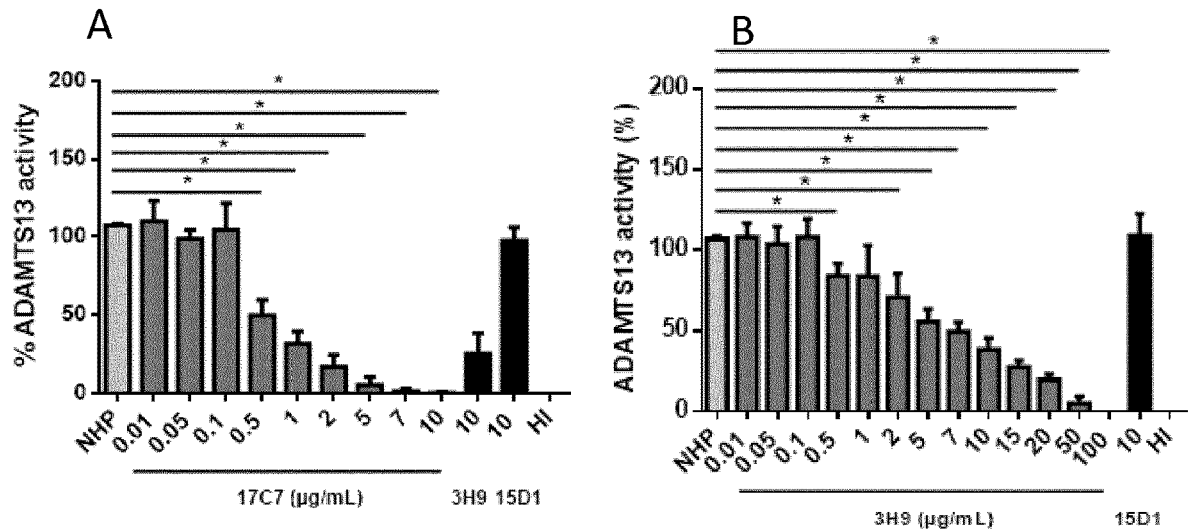
Figure 12:
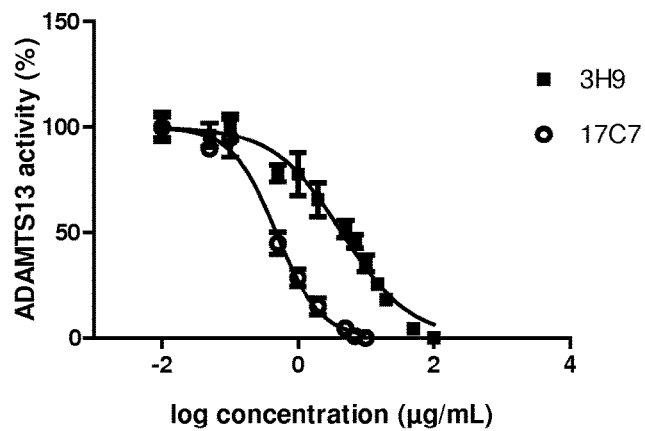

FIGS. 11A and 11B and FIG. 12 show the inhibitory effect of the 17C7 and 3H9 (Ab11316CB) antibody on ADAMTS13 activity.

Figure 13:
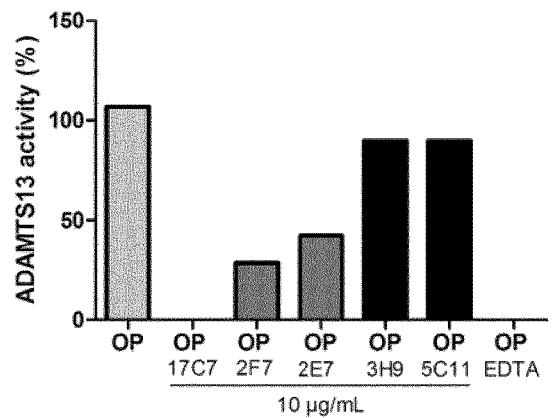

FIG. 13 shows the cross reactivity of the 17C17 antibody with sheep ADAMTS13 via inhibition of sheep ADAMTS13 activity.

FIGS. 14A and 14B show a dose response of the inhibitory effect of the 17C17 antibody on sheep ADAMTS13 activity.

FIGS. 15A and 15B show the determination of vWF multimers before and after LVAD implantation in sheep.

Figure 16:
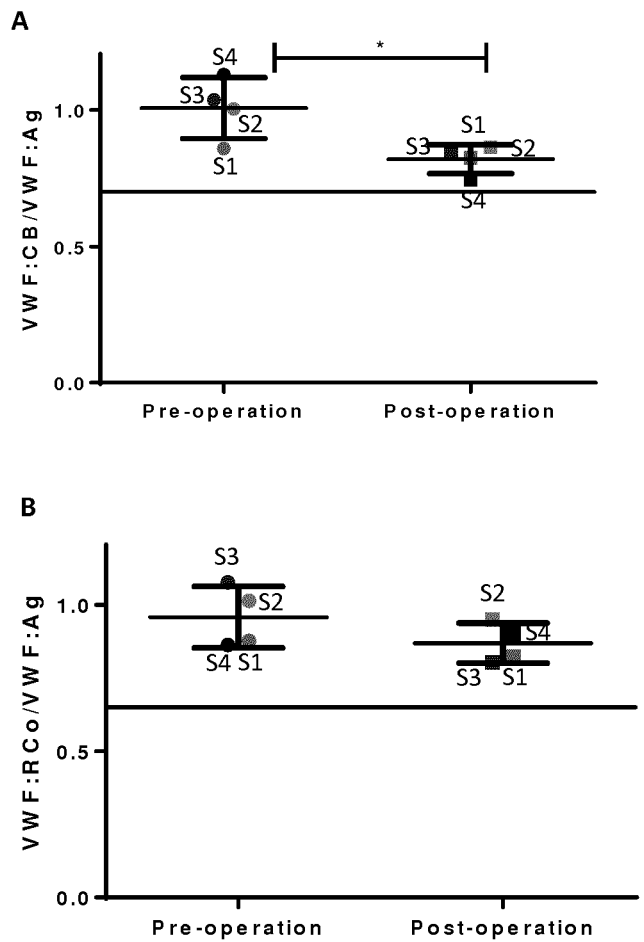

FIGS. 16A and 16B show collagen binding and ristocetin cofactor activity of VWF before and after implantation of an LVAD.

Figure 17:
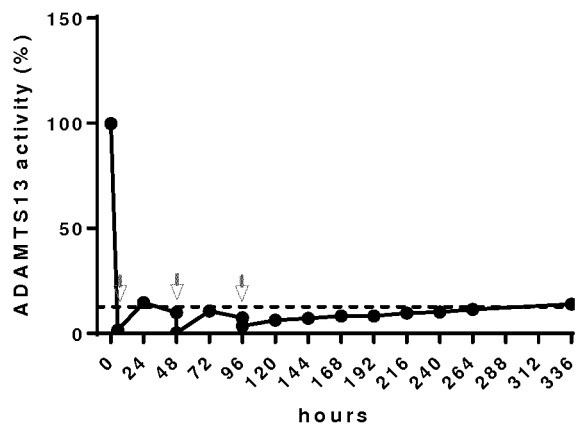

FIG. 17 shows the in vivo inhibition of sheep ADAMTS13 by the 17C7 antibody.

Figure 18:
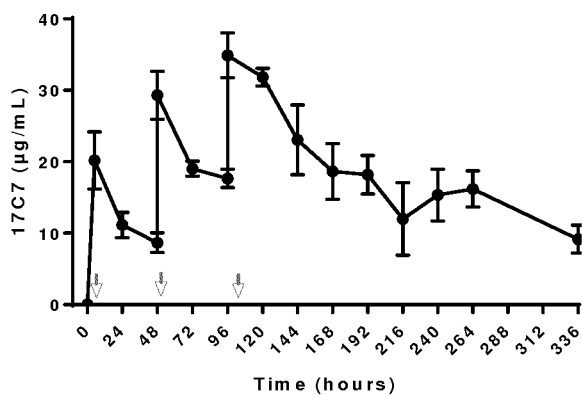

FIG. 18 shows antibody plasma levels of the 17C7 antibody in sheep.

Figure 19:
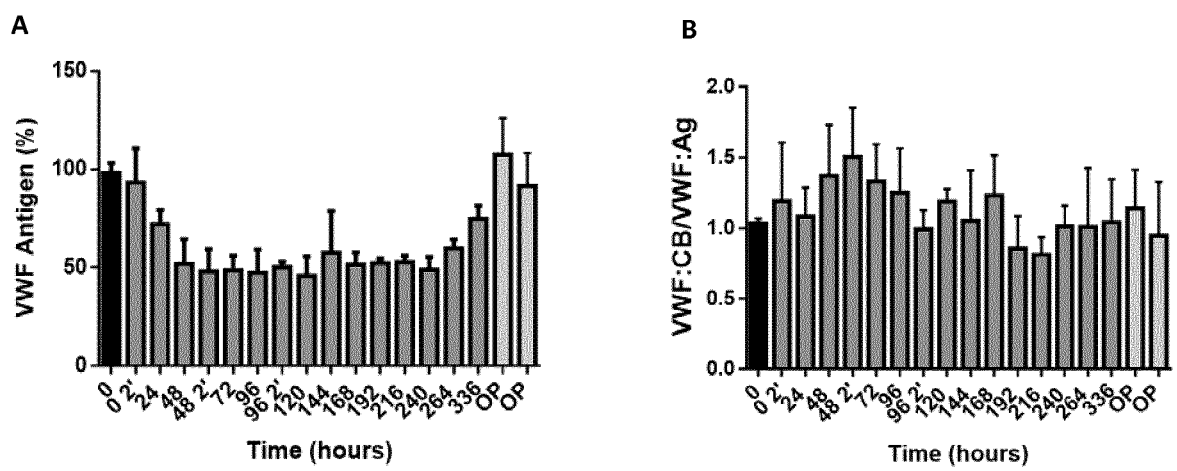

FIGS. 19A and 19B show the VWF antigen levels and VWF collagen binding activity of sheep injected with the 17C7 antibody.

Figure 20:
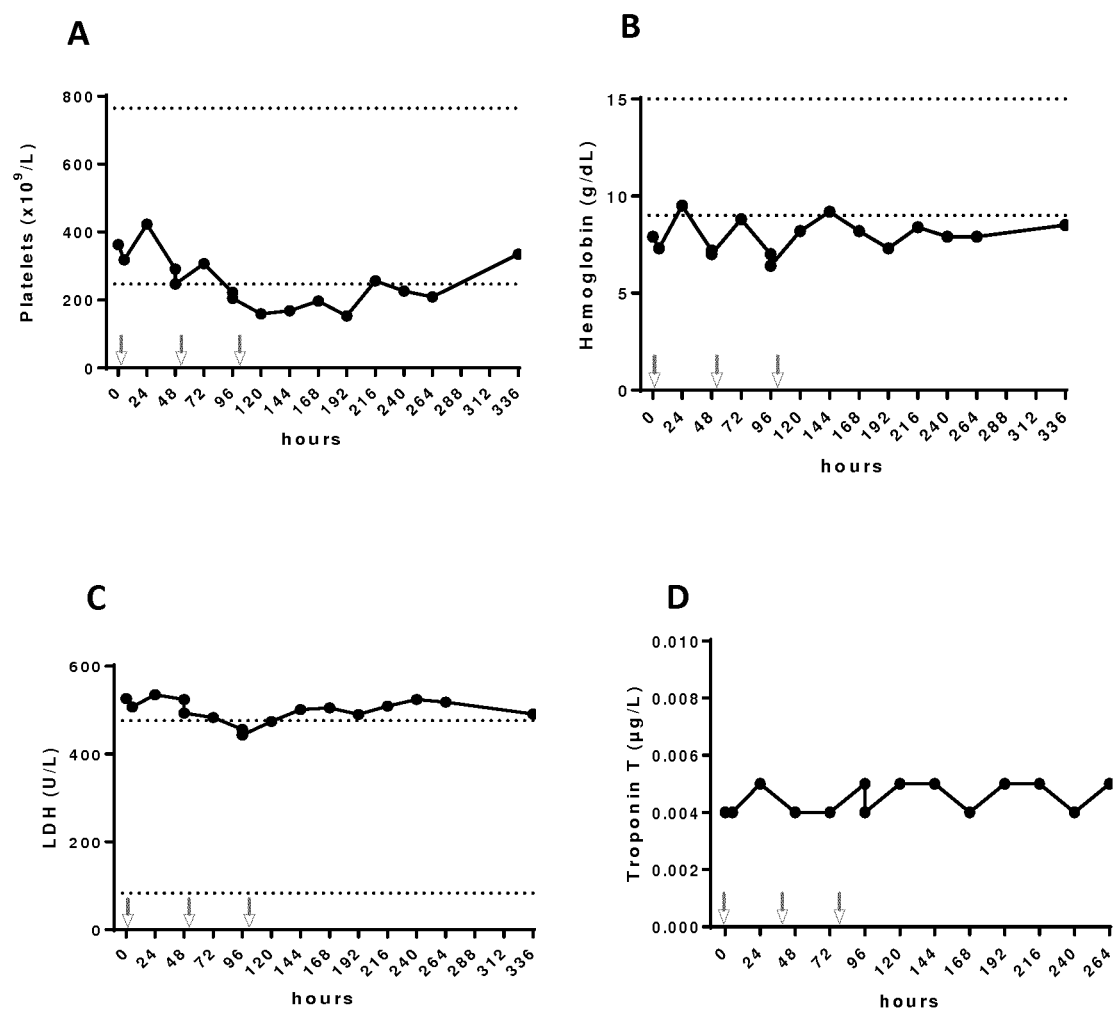
Figure 20:
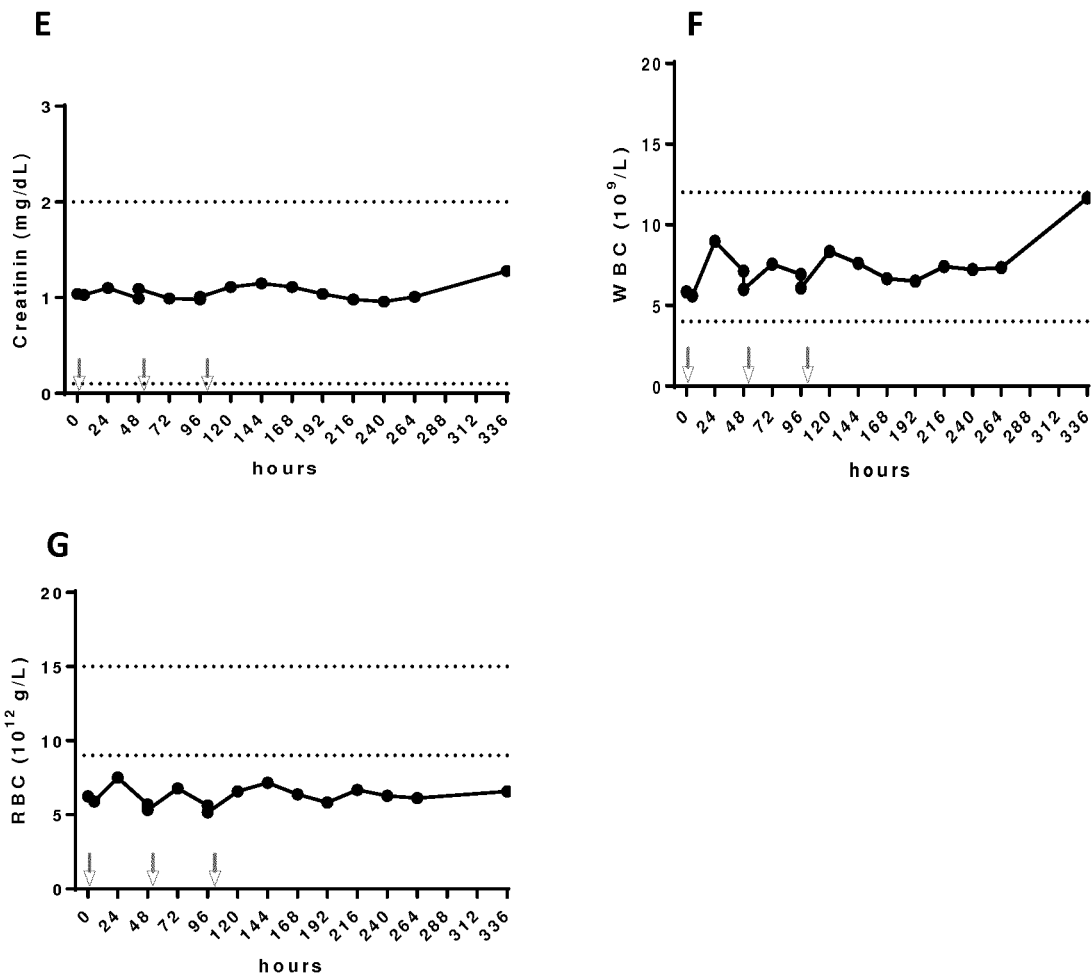

FIGS. 20 A to 20G show various haematological parameters after injection with the 17C7 antibody.

DETAILED DESCRIPTION

The following detailed description of the invention refers to the accompanying drawings. The same reference numbers in different drawings identify the same or similar elements. Also, the following detailed description does not limit the invention. Instead, the scope of the invention is defined by the appended claims and equivalents thereof.

Several documents are cited throughout the text of this specification. Each of the documents herein (including any manufacturer's specifications, instructions etc.) are hereby incorporated by reference; however, there is no admission that any document cited is indeed prior art of the present invention.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn to scale for illustrative purposes. The dimensions and the relative dimensions do not correspond to actual reductions to practice of the invention.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to the devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Other embodiments of the invention will be apparent to those skilled in the art from consideration of the specification and practice of the invention disclosed herein.

It is intended that the specification and examples be considered as exemplary only.

Each and every claim is incorporated into the specification as an embodiment of the present invention. Thus, the claims are part of the description and are a further description and are in addition to the preferred embodiments of the present invention.

The following terms are provided solely to aid in the understanding of the invention.

Particular and preferred aspects of the invention are set out in the accompanying independent and dependent claims. Features from the dependent claims may be combined with features of the independent claims and with features of other dependent claims as appropriate and not merely as explicitly set out in the claims.

Thus, the claims following the detailed description are hereby expressly incorporated into this detailed description, with each claim standing on its own as a separate embodiment of this invention.

As used in the specification and the attached claims, the use of "a," "an" and "the" include references to plural subject matter referred to unless the context clearly dictates otherwise. Thus, for example, reference to "a protein" includes a single catalyst as well as a combination or mixture of two or more proteins, reference to "an antigen" encompasses a combination or mixture of different antigens as well as a single antigen, and the like.

A term which is subsumed under another term may be embraced by the broader term or by the more narrow specific term as appropriate within the context of the use of that term. All terms used to describe the present invention are used within context.

Except when noted, the terms "patient" or "subject" are used interchangeably and refer to a human patient.

Examples of dosage ranges that can be administered to a subject can be chosen from: 1 µg/kg to 20 mg/kg, 1 µg/kg to 10 mg/kg, 1 µg/kg to 1 mg/kg, 10 µg/kg to 1 mg/kg, 10 µg/kg to 100 µg/kg, 100 µg/kg to 1 mg/kg, 250 µg/kg to 2 mg/kg, 250 µg/kg to 1 mg/kg, 500 µg/kg to 2 mg/kg, 500 µg/kg to 1 mg/kg, 1 mg/kg to 2 mg/kg, 1 mg/kg to 5 mg/kg, 5 mg/kg to 10 mg/kg, 10 mg/kg to 20 mg/kg, 15 mg/kg to 20 mg/kg, 10 mg/kg to 25 mg/kg, 15 mg/kg to 25 mg/kg, 20 mg/kg to 25 mg/kg, and 20 mg/kg to 30 mg/kg (or higher). These dosages may be administered daily, weekly, biweekly, monthly, or less frequently, for example, biannually, depending on dosage, method of administration, disorder or symptom(s) to be treated, and individual subject characteristics. Dosages can also be administered via continuous infusion (such as through a pump). The administered dose may also depend on the route of administration. For example, subcutaneous administration may require a higher dosage than intravenous administration.

In certain circumstances, it may be advantageous to formulate compositions in dosage unit form for ease of administration and uniformity of dosage. Dosage unit form as used herein refers to physically discrete units suited for the patient. Each dosage unit contains a predetermined quantity of antibody calculated to produce a therapeutic effect in association with the carrier. The dosage unit depends on the characteristics of the antibodies and the particular therapeutic effect to be achieved.

Toxicity and therapeutic efficacy of the composition can be determined by standard pharmaceutical procedures in cell cultures or experimental animals, e.g., determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Antibodies that exhibit large therapeutic indices may be less toxic and/or more therapeutically effective.

The data obtained from the cell culture assays and animal studies can be used to formulate a dosage range in humans. The dosage of these compounds may lie within the range of circulating antibody concentrations in the blood, that includes an ED50 with little or no toxicity. The dosage may vary within this range depending upon the dosage composition form employed and the route of administration. For any antibody used in the present invention, the therapeutically effective dose can be estimated initially using cell culture assays. A dose may be formulated in animal models to achieve a circulating plasma concentration range that includes the IC50 (i.e., the concentration of antibody which achieves a half-maximal inhibition of symptoms).

The terms "treating" or "treatment" include the administration of the compounds or agents of the present invention to prevent or delay the onset of the symptoms, complications, or biochemical indicia of a disease, alleviating the symptoms or arresting or inhibiting further development of the disease, condition, or disorder (e.g., LVAD induced bleeding disorder). Treatment may be prophylactic (to prevent or delay the onset of the disease, or to prevent the manifestation of clinical or subclinical symptoms thereof) or therapeutic suppression or alleviation of symptoms after the manifestation of the disease.

As used herein, "circulatory assist device" means mechanical circulatory assist (support) devices designed to be used for a wide range of clinical conditions ranging from prophylactic insertion for high-risk invasive coronary artery procedures to the management of cardiogenic shock, acute decompensated heart failure, or cardiopulmonary arrest. There are four major (arbitrary) categories of circulatory assist devices: intra-aortic balloon pump (IABP), non-IABP percutaneous mechanical circulatory assist devices, extracorporeal membrane oxygenator pumps, and nonpercutaneous centrifugal pumps, which are used for cardiopulmonary bypass.

Non-IABP percutaneous mechanical circulatory assist devices comprise continuous flow pumps. In the literature, these devices have differing names: percutaneous ventricular assist devices, percutaneous ventricular support devices, percutaneous mechanical circulatory assist devices, percutaneous mechanical circulatory support devices, and percutaneous ventricular assist devices (VADs). A ventricular assist device (VAD) is a mechanical pump that's used to support heart function and blood flow in people who have weakened hearts. This mechanical pump that is implanted inside a person's chest to help a weakened heart pump blood throughout the body. The device takes blood from a lower chamber of the heart and helps pump it to the body and vital organs, just as a healthy heart would. VADs are designed to assist either the right (RVAD) or left (LVAD) ventricle, or both at once (BiVAD). The type that is used depends primarily on the underlying heart disease and the pulmonary arterial resistance that determines the load on the right ventricle. LVADs are most commonly used, but when pulmonary arterial resistance is high, right ventricular assistance may become necessary. Unlike a total artificial heart, the LVAD doesn't replace the heart; it supports the heart. This can mean the difference between life and death for a person whose heart needs a rest after open-heart surgery, or for some patients waiting for a heart transplant (called "bridge to transplant"). LVADs may also be used as "destination therapy," which is an alternative to transplant. Destination therapy is used for long-term support in some terminally ill patients whose condition makes them ineligible for heart transplantation. An example of an LVAD is the HeartMate II® Left Ventricular Assist System (Thoratec Corporation, USA). Another example is the Impella micro-axial flow device, which is an axial flow pump which works on the principle of an Archimedes screw. The inflow is placed retrograde across the aortic valve into the left ventricle. A pump revolving at high speeds draws blood out of the left ventricle and ejects it into the ascending aorta beyond the end of the pump. Another example of a left ventricle assist device is described and displayed in U.S. Pat. No. 7,846,083.

Such mechanical circulatory support may be considered in particular clinical situations such as 1) Very high-risk percutaneous coronary intervention, including those with complex coronary artery disease involving a large territory and severe left ventricular dysfunction (ejection fraction<35 percent) or recent decompensated heart failure, 2) Complications of acute myocardial infarction, including cardiogenic shock with or without mechanical defects such as ischemic mitral regurgitation or ventricular septal rupture, 3) Advanced heart failure (during the period of stabilization of a critically ill patient while making decisions about longer-term support ("bridge-to-a-bridge")), 4) Support during high-risk percutaneous valve procedures, 5) Support for patients referred for electrophysiologic procedures with severe underlying left ventricular dysfunction who may not tolerate sustained ventricular arrhythmias during the procedure, 6) Patients with medically refractory (particularly ventricular) arrhythmias associated with ischemic and acute cardiac allograft failure or post-transplant right ventricular failure.

There is a risk of internal bleeding due to the circulatory assist device immediately after implant and during support, and episodes of post-implantation bleeding. Bleeding is the most common complication associated with the placement of a circulatory assist device and in particular of a ventricular assist device such as a LVAD. In the early experience with pulsatile LVADs, as many as 50% of patients required reoperation for bleeding. These bleeding disorders are due to the circulatory assist device placement but the mechanism is not fully understood and several causes are provided. It could be related to the effects of blood interaction with the VAD surface, to high shear stress which has previously been noted to alter the 3-dimensional structure of VWF and to enhance proteolysis of VWF by ADAMTS13, to increased platelet damage and activation, and/or to elevated platelet, leukocyte, and endothelial cell-derived microparticles in patients after VAD, indicating enhanced vascular inflammation and procoagulation.

Despite >2 decades of experience with LVADs, the incidence of major bleeding is currently still >20%. More important, newer CF pumps require anticoagulation, thereby significantly increasing bleeding-related complications at the time of cardiac transplantation and LVAD explantation, and imposing a bleeding risk throughout the duration of LVAD support.

The ADAMTS13 inhibition therapy of the present invention is to prevent or treat such bleeding disorder by ADAMTS13 antibodies, antibody-like scaffolds and antibody fragments.

Further, the methods and compounds of the present invention can be used to treat or prevent haemorrhagic complications or bleeding disorders caused by high shear stress in patients without implanted LVAD like patients suffering from Heyde's syndrome and patients with a veno-venous Extra Corporeal Membrane Oxygenation support (ECMO) for respiratory support.

The present invention provides isolated ADAMTS13 antibodies, antibody-like scaffolds and antibody fragments, characterized in that they preferentially bind to ADAMTS13.

As used herein, "ADAMTS13" shall mean "A Disintegrin And Metalloproteinase With A Thrombospondin Type 1 Motif, Member 13", also known as von Willebrand factor-cleaving protease (VWFCP). The amino acids sequence of human ADAMTS13 isoform 1 is deposited as uniprot entry Q76LX8, of human ADAMTS13 isoform 2 deposited as uniprot entry Q76LX8-2, of human ADAMTS13 isoform 3 deposited as uniprot entry Q76LX8-3 and of human ADAMTS13 isoform 4 deposited as uniprot entry Q76LX8-4.

As used herein, "VWF" shall mean "Von Willebrand factor", a blood glycoprotein involved in haemostasis.

The sequence of human VWF is deposited as uniprot entry P04275, isoform 2 is deposited as P04275-2.

It is deficient or defective in von Willebrand disease and is involved in a large number of other diseases, including thrombotic thrombocytopenic purpura, Heyde's syndrome, and inflammation. Increased plasma levels in a large number of cardiovascular, neoplastic, and connective tissue diseases are presumed to arise from adverse changes to the endothelium, and may contribute to an increased risk of thrombosis.

By "ADAMTS13 antibody" and "ADAMTS13 antibody fragment" are meant an antibody and antibody fragment, respectively, that binds to ADAMTS13. The ADAMTS13 antibodies and ADAMTS13 antibody fragments of the invention are thus antibodies and antibody fragments that specifically bind ADAMTS13. Furthermore, these antibodies and fragments inhibit proteolytic cleavage of VWF by ADAMTS13

The phrase "specifically bind(s)" or "bind(s) specifically" when referring to a peptide, refers to a peptide molecule which has intermediate or high binding affinity, exclusively or predominately, to a target molecule. The phrases "specifically binds to" refers to a binding reaction which is determinative of the presence of a target protein in the presence of a heterogeneous population of proteins and other biologics. Thus, under designated assay conditions, the specified binding moieties bind preferentially to a particular target protein and do not bind in a significant amount to other components present in a test sample. Specific binding to a target protein under such conditions may require a binding moiety that is selected for its specificity for a particular target antigen. A variety of assay formats may be used to select ligands that are specifically reactive with a particular protein, for example, solid-phase ELISA immunoassays, or immunoprecipitation. Typically, a specific or selective reaction will be at least twice background signal or noise and more typically more than 10 times background. For instance, antibodies and antibody fragments of the invention preferentially bind to ADAMTS13, whereby by "preferentially binding", "preferentially recognizing" or "preferentially reacting with" is meant that the antibodies or antibody fragments show greater binding capacity for ADAMTS13 as compared to any other antigen. The binding capacity of an antibody or antibody fragment to an antigen is reflective of its affinity and/or avidity for that antigen.

Binding Specificity can be Expressed by Association and Dissociation Constants as Determined by ELISA or BIA-CORE The terms "antibody" and "antibodies" are recognized in the art and refer to proteins also known as immunoglobulins that bind to antigens. It is to be understood that these terms encompass conventional vertebrate antibodies like IgA, IgD, IgE, IgG, IgM, IgT, IgX and IgY, composed of at least two heavy and two light chains, as well as antibodies only composed of two heavy chains (VHH antibodies, IgNAR, heavy-chain antibodies, single-domain antibodies or nanobodies), and single-chain antibodies. In the case of conventional antibodies, the antigen binding sites are contributed to by the variable domains of both the heavy and light chains (VH and VL). The term "variable domain" refers to the part or domain of an antibody which is partially or fully responsible for antigen binding. Generally, variable domains will be amino acid sequences that essentially consist of 4 framework regions (FR1 to FR4 respectively) and 3 complementarity determining regions (CDR1 to CDR3 respectively), or any suitable fragment of such an amino acid sequence which usually contains at least some of the amino acid residues that form at least one of the CDR's. Such variable domains and fragments are most preferably such that they comprise an immunoglobulin fold or are capable for forming, under suitable conditions, an immunoglobulin fold. Each CDR may contribute to a greater or lesser extent to antigen binding by the antibody. Single domain antibodies or heavy-chain antibodies can be found in camelids and sharks, and each of the antigen-binding sites of these antibodies is formed by a single heavy chain variable domain (VHH) only. Therefore, only three CDRs contribute to a greater or lesser extent to each antigen-binding site. Single chain antibodies (scFv) are derived from conventional antibodies by translational fusion of the VH and VL domains, separated by a flexible linker, into a single antigen-binding domain. Framework sequences of an antibody may be altered without altering the antigenic specificity of the antibody, or in order to change the binding affinity of the antibody. Furthermore, conventional antibodies may switch classes or isotypes without substantially affecting antigen-binding characteristics.

The term "complementarity determining region" or "CDR" refers to variable regions of either H (heavy) or L (light) chains (abbreviated as VH and VL, respectively) and contains the amino acid sequences capable of specifically binding to antigenic targets. These CDR regions account for the specificity of the antibody for a particular antigenic determinant structure. Such regions are also referred to as "hypervariable regions." The CDRs represent non-contiguous stretches of amino acids within the variable regions but, regardless of species, the positional locations of these critical amino acid sequences within the variable heavy and light chain regions have been found to have similar locations within the amino acid sequences of the variable chains. The accepted CDR regions and variable domains of an antibody are known to the skilled person and have been described by (Kabat E A et al. (1991) Sequences of proteins of immunological interest, 5th edn. U.S. Department of Health and Human Services, National Institutes for Health, Bethesda, Md.) and (Padlan et al., (1995) Identification of specificity-determining residues in antibodies. *FASEB J.* 9, 133-139).

The skilled person is familiar with the concept that, upon alignment of corresponding CDRs of different antibodies with similar antigen specificity, the positions in the alignment which are conserved, i.e. identical in all sequences in the alignment, are critical for the antigen specificity of the antibodies. The residues of a particular CDR at these critical positions are known as "specificity-determining residues" or "SDRs". As a consequence, positions which are not conserved contribute less to the specificity of the antibodies and can be substituted without substantially affecting the antigen specificity of an antibody. Therefore, the skilled person is able to determine which residues could be substituted without substantially affecting antigen specificity of the antibody or antibody fragment. In the same way, the skilled person is able to determine the minimum sequence identity between a particular CDR of an antibody and the corresponding CDR of an antibody of the present invention, which is required for the particular CDR to have a similar antigen specificity as the corresponding CDR of an antibody of the present invention. The same holds true for the variable regions.

By the term "antibody fragment" is meant a fragment of an antibody that largely retains antigen-binding capacity of the antibody from which it is derived. Therefore, an ADAMTS13 antibody fragment of the invention is capable of preferentially binding to ADAMTS13. Antigen-binding capacity is determined by the variable domain or domains, more particularly by 1, 2, 3, 4, 5 or 6 CDRs located in the VH and/or VL domains in the case of conventional and single-chain antibodies, and 1, 2 or 3 CDRs in the case of single-domain antibodies. Preferred antibody fragments of the invention therefore comprise antigen-binding sites comprising 1, 2, 3, 4, 5 or 6 CDRs. Two or more CDRs may be physically separated from each other by connecting regions to provide a framework structure for the CDRs. More preferred antibody fragments of the invention comprise antigen-binding sites comprising 1 or 2 variable domains. Examples of antibody fragments are well-known to the skilled person and include the monovalent antigen-binding fragments (Fab), bivalent F(ab') 2 fragments, Fv fragments (e.g. single chain antibodies scFv), miniaturized antibodies, single-domain antibody fragments like nanobodies (Nelson Ala. 2010, Antibody fragments: hope and hype. mAbs 2:77-83). Antibody fragments of the invention may be obtained by enzymatic or chemical proteolysis, or by recombinant DNA technology techniques well known to the skilled person.

Antibodies and antibody fragments of the invention may be further chemically conjugated, non-covalently bound, or translationally fused to other proteins. Single chain antibodies scFv are an example of translational fusion between a VH and a VL domain. Further examples are albumin-conjugated antibodies or antibody fragments, bivalent diabodies, and monospecific and bispecific tandem svFcs (Nelson Ala. 2010, Antibody fragments: hope and hype. mAbs 2:77-83).

A single-chain antibody (also referred to as "scFv") can be prepared by linking a heavy chain V region and a light chain V region of an antibody (for a review of scFv see Pluckthun "The Pharmacology of Monoclonal Antibodies" Vol. 113, eds. Rosenburg and Moore, Springer Verlag, New York, pp. 269-315 (1994)). Methods for preparing single-chain antibodies are known in the art (see, for example, U.S. Pat. Nos. 4,946,778, 5,260,203, 5,091,513, and 5,455,030). In such scFvs, the heavy chain V region and the light chain V region are linked together via a linker, preferably, a polypeptide linker (Huston, J. S. et al., Proc. Natl. Acad. Sci. U.S.A, 1988, 85, 5879-5883). The heavy chain V region and the light chain V region in a scFv may be derived from the same antibody, or from different antibodies.

An "Fv" fragment is the smallest antibody fragment, and contains a complete antigen recognition site and a binding site. This region is a dimer (VH-VL dimer) wherein the variable regions of each of the heavy chain and light chain are strongly connected by a noncovalent bond. The three CDRs of each of the variable regions interact with each other to form an antigen binding site on the surface of the VH-VL dimer. In other words, a total of six CDRs from the heavy and light chains function together as an antibody's antigen-binding site. However, a variable region (or a half Fv, which contains only three antigen-specific CDRs) alone is also known to be able to recognize and bind to an antigen, although its affinity is lower than the affinity of the entire binding site. Thus, a preferred antibody fragment of the present invention is an Fv fragment, but is not limited thereto.

Such an antibody fragment may be a polypeptide which comprises an antibody fragment of heavy or light chain CDRs which are conserved, and which can recognize and bind its antigen.

A Fab fragment (also referred to as F(ab)) also contains a light chain constant region and heavy chain constant region (CH1). For example, papain digestion of an antibody produces the two kinds of fragments: an antigen-binding fragment, called a Fab fragment, containing the variable regions of a heavy chain and light chain, which serve as a single antigen-binding domain; and the remaining portion, which is called an "Fc" because it is readily crystallized. A Fab' fragment is different from a Fab fragment in that a Fab' fragment also has several residues derived from the carboxyl terminus of a heavy chain CH1 region, which contains one or more cysteine residues from the hinge region of an antibody.

A Fab' fragment is, however, structurally equivalent to Fab in that both are antigen-binding fragments which comprise the variable regions of a heavy chain and light chain, which serve as a single antigen-binding domain. Herein, an antigen-binding fragment comprising the variable regions of a heavy chain and light chain which serve as a single antigen-binding domain, and which is equivalent to that obtained by papain digestion, is referred to as a "Fab-like antibody", even when it is not identical to an antibody fragment produced by protease digestion. Fab'-SH is Fab' with one or more cysteine residues having free thiol groups in its constant region. A F(ab') fragment is produced by cleaving the disulfide bond between the cysteine residues in the hinge region of F(ab')2. Other chemically crosslinked antibody fragments are also known to those skilled in the art.

Pepsin digestion of an antibody yields two fragments; one is a F(ab')2 fragment which comprises two antigen-binding domains and can cross-react with antigens, and the other is the remaining fragment (referred to as pFc'). Herein, an antibody fragment equivalent to that obtained by pepsin digestion is referred to as a "F(ab')2-like antibody" when it comprises two antigen-binding domains and can cross-react with antigens. Such antibody fragments can also be produced, for example, by genetic engineering. Such antibody fragments can also be isolated, for example, from the antibody phage library described above. Alternatively, F(ab')2-SH fragments can be recovered directly from hosts, such as *E. coli*, and then allowed to form F(ab')2 fragments by chemical crosslinking (Carter et al., *Bio/Technology* 10:163-167 (1992)).

Antibodies and antibody fragments of the invention may be further modified. Examples of such modifications include the addition of detectable enzymatic, fluorescent, luminescent, or radioactive marker groups or molecules that act in detection such as streptavidin. Other examples include the chemical modification to alter the half-life of antibodies and antibody fragments, such as PEGylation. Still other examples add effector moieties to antibodies and antibody fragments, such as toxins, radioisotopes, enzymes, cytokines, and antigens (Nelson Ala. 2010, Antibody fragments: hope and hype. mAbs 2:77-83).

Antibodies or antibody fragments may be further modified into an antibody-derived scaffold or antibody-like scaffolds that largely retains antigen-binding capacity of the antibody or antibody fragments from which it is derived. Examples of antibody-derived scaffolds or antibody-like scaffolds are domain antibodies (dAb) that selectively or preferentially bind the same epitope as a natural antibody, for instance dAb with fully human frameworks, for instance dAb fused to a human Fc domain or for instance nanobodies engineered in a molecule that has an IgG-like circulating half-life in humans or antibody fragments with retained antigen-binding capacity or domain antibody with active scaffolds for controlled and cell delivery.

Single domain antibodies can be engineered into antibody like fragments. Single domain antibodies are antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, goat, rabbit, bovine. According to one aspect of the invention, a single domain antibody as used herein is a naturally occurring single domain antibody known as heavy chain antibody devoid of light chains. Such single domain antibodies are disclosed in WO9404678 for example. For clarity reasons, this variable domain derived from a heavy chain antibody naturally devoid of light chain is known herein as a VHH or nanobody to distinguish it from the conventional VH of four chain immunoglobulins. Such a VHH molecule can be derived from antibodies raised in Camelidae species, for example in camel, llama, dromedary, alpaca and guanaco or Elasmobranchii species for instance skates, rays (batoidea), and sharks (selachii). Other species besides Camelidae may produce heavy chain antibodies naturally devoid of light chain; such VHHs are within the scope of the invention. The single-chain polypeptide may be produced by various methods well known in the art such as genetic engineering technique and chemical synthesis. The genetic engineering technique includes constructing a replicable cloning vector or expression vector, transforming the host cell with the vector, culturing the transformed host cell to express the nucleic acid in it, collecting and purifying the single-chain polypeptide. The vector usually comprises the nucleic acid encoding one of the two single-chain polypeptides constituting the diabody-type bispecific antibody according to the present invention. In such case, the resulting two kinds of the vectors are preferably introduced into the same host cell.

Alternatively, the two kinds of nucleic acid encoding the different single-chain polypeptides from each other may be comprised in the same vector. The term "replicable expression vector" or "expression vector" as used herein refers to a piece of DNA (usually double-stranded) that may comprise a fragment of a foreign DNA fragment inserted therein. The foreign DNA is also defined as a "heterologous DNA", which cannot be found naturally in a host cell in interest. The vector is used to carry or convey the foreign or heterologous DNA into an appropriate host cell. Once the vector is introduced into the host cell, it may be replicated independently from a chromosomal DNA of the host cell to produce copies of the vector and foreign DNA inserted therein. The vector also comprises elements essential for translating the foreign DNA into a polypeptide so that the polypeptide molecules encoded by the foreign DNA will be synthesized very quickly.

The above vector means a DNA construct comprising an appropriate control sequence and DNA sequence that are operably linked together (i.e., linked together so that the foreign DNA can be expressed). The control sequence includes a promoter for transcription, an optional operator sequence to regulate the transcription, a sequence encoding an appropriate mRNA ribosome-biding site, an enhancer, a polyadenylation sequence, and a sequence controlling the termination of transcription and translation. The vector may further comprise various sequences known in the art, such as a restriction enzyme cleaving site, a marker gene (selection gene) such as a drug-resistant gene, a signal sequence, and a leader sequence. These sequences and elements may be optionally selected by those skilled in the art depending on the kinds of the foreign DNA and host cell, and conditions of culture medium.

The vector may be in any form such as a plasmid, phage particle, or just simply genomic insert. Once the appropriate host cell is transformed with the vector, the vector will be replicated or function independently from the genome of the host cell, or the vector will alternatively be integrated into the genome of the cell. Any cell known in the art may be used as the host cell, for example, there may be mentioned procaryotic cells such as including *E. coli*, eucaryotic cells such as mammalian cells such Chinese hamster ovary (CHO) cell and human cells, yeast, and insect cells.

Although the single-chain polypeptide obtained by the expression in the host cell is usually secreted and collected from the culture medium, it may be also collected from cell lysate when it is directly expressed without a secretion signal. In case the single-chain polypeptide has a membrane-binding property, it may be released from the membrane with an appropriate surfactant such as Triton-X100.

Purification of the polypeptide may be carried out by any method known to those skilled in the art such as centrifugation, hydroxyapatite chromatography, gel electrophoresis, dialysis, separation on ion-exchange chromatography, ethanol precipitation, reverse phase HPLC, silica chromatography, heparin-sepharose chromatography, anion- or cation-resin chromatography such as polyaspartic acid column, chromato-focusing, SDS-PAGE, precipitation with ammonium sulfate, and affinity chromatography. The affinity chromatography, which utilizes affinity with a peptide tag of the single-chain polypeptide, is one of the preferred purification techniques with a high efficiency.

Since the collected single-chain polypeptide may be often included in an insoluble fraction, the polypeptide is preferably purified after being solubilized and denatured. The solubilization treatment may be carried out with the use of any agent known in the art, including alcohol such as ethanol, a dissolving agent such as guanidine hydrochloride and urea.

The antibody-like fragments according to the present invention are produced by assembling the single-chain polypeptides, eventually on a scaffold, and separating and collecting the thus formed antibody-like fragments.

Assembling treatment brings the single-chain polypeptides back in an appropriate spatial arrangement in which a desired biological activity is shown. Thus, since this treatment brings the polypeptides or domains back into an assembling state, it may be considered "re-assembling." It may be also called "re-constitution" or "refolding" in view of gaining the desired biological activity.

The assembling treatment may be carried out by any method known in the art preferably by gradually lowering the concentration of a denaturing agent such as guanidine hydrochloride in a solution comprising the single-chain polypeptide by means of dialysis. During these processes, an anti-coagulant or oxidizing agent may be optionally added in a reaction system in order to promote the oxidation. The separation and collection of the formed antibody-like fragment may be done by any method known in the art as well.

VHHs, according to the present invention, and as known to the skilled addressee, are heavy chain variable domains derived from immunoglobulins naturally devoid of light chains such as those derived from Camelidae as described in WO9404678 (and referred to hereinafter as VHH domains or nanobodies). VHH molecules are about 10× smaller than IgG molecules. They are single polypeptides and very stable, resisting extreme pH and temperature conditions. Moreover, they are resistant to the action of proteases which is not the case for conventional antibodies. Furthermore, in vitro expression of VHHs produces high yield, properly folded functional VHHs. In addition, antibodies generated in Camelids will recognize epitopes other than those recognised by antibodies generated in vitro through the use of antibody libraries or via immunisation of mammals other than Camelids or Elasmobranchii species (WO 9749805). As such, anti-albumin VHH's may interact in a more efficient way with serum albumin which is known to be a carrier protein. As a carrier protein some of the epitopes of serum albumin may be inaccessible by bound proteins, peptides and small chemical compounds. Since VHH's are known to bind into 'unusual' or non-conventional epitopes such as cavities (WO9749805), the affinity of such VHH's to circulating albumin may be increased.

In one embodiment, the antibodies and antibody fragments of the invention are humanized. Antibody fragments derived from an antibody of the invention can be fused to the Fc region of a human antibody, in order to obtain humanized antibodies and antibody fragments. Humanized antibodies or antibody fragments can also be obtained by grafting of one or more CDRs or only their specificity-determining residues (SDRs), optionally together with one or more framework residues important for optimal CDR functionality, of a non-human antibody having the desired antigen-binding specificity, into framework polypeptide sequences of a human antibody or antibody fragment, or even into a universal humanized nanobody scaffold. Methods to humanize antibodies are well known to those skilled in the art (see e.g. (De Pascalis et al., *J Immunol.* 169:6, 3076-3084 (2002); Kashmiri et al., *Methods,* 36:25-34 (2005); Almagro and Fransson, Front. Biosci., 13:1619-1633 (2008); Vincke, et al., J Biol Chem., 284:3273-3284 (2009); Borras et al. *J Biol Chem.* 19(285):9054-9066 (2010); Harding et al., *Mabs,* 2:256-265 (2010)).

The term "humanized antibody" as used herein means a human immunoglobulin (a recipient antibody) in which at least part of the residues of complementary-determining region (CDR) is replaced with residues derived from the CDR of a non-human animal antibody (a donor antibody) that has a desired specificity, affinity and capability, such as those of mouse, rat, and rabbit. In some cases, the residue(s) of a Fv framework (FR) in the human immunoglobulin is replaced with residue(s) of the corresponding non-human antibody. The humanized antibody may further comprise a residue that is not found in the recipient antibody or the introduced CDR or framework. These changes are made in order to optimize or improve the properties of the resulting antibody. More detailed information on these changes are referred to Jones et al., *Nature,* 321:522-525 (1986); Reichmann et al., *Nature,* 332:323-329 (1988); EP0239400B; Presta, *Curr. Op. Struct. Biol,* 2:593-596 (1992); and EP0451216B.

The antibody fragments of the present invention can also be generated using various phage display methods known in the art. In phage display methods, functional antibody domains are displayed on the surface of phage particles which carry the polynucleotide sequences encoding them. In particular, such phage can be utilized to display epitope-binding domains expressed from a repertoire or combinatorial antibody library (e.g., human or murine). Phage expressing an epitope-binding domain that binds the antigen of interest can be selected or identified with antigen, e.g., using labeled antigen bound or captured to a solid surface or bead. Phages used in these methods are typically filamentous phage including fd and M13 binding domains expressed from phage with antigen-binding antibody domains recombinantly fused to either the phage gene III or gene VIII protein. Examples of phage display methods that can be used to make the antibodies or antibody fragments of the present invention include those disclosed in (Kettleborough et al *Eur. J. Immunol.,* 24:952-958 (1994); Burton et al., *Advances in Immunology,* 57: 191-280 (1994); Brinkman et al., *J. Immunol. Methods,* 182: 41-50 (1995); Ames et al., *J. Immunol. Methods,* 184: 177-186 (1995); Persic et al., *Gene,* 187: 9-18 (1997); WO/1992/001047; WO 90002809; WO 91/10737; WO 92/01047; WO 92/18619; WO 93/11236; WO 95/15982; WO 95/20401; and U.S. Pat. No. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108).

After phage selection, the regions of the phage encoding the fragments can be isolated and used to generate the epitope-binding fragments through expression in a chosen host, including mammalian cells, insect cells, plant cells, yeast, and bacteria, using recombinant DNA technology. For example, techniques to recombinantly produce antigen-binding fragments can also be employed using methods known in the art such as those disclosed in WO 92/22324; Better et al., *Science,* 240: 1041-1104 (1988); Mullinax et al., Biotechniques, 12(6):864-869 (1992); Sawai et al., *AJRI,* 34:2634 (1995). Examples of techniques which can be used to produce single-chain Fvs and antibodies include those described in U.S. Pat. Nos. 4,946,778 and 5,258,498; Skerra et al., *Science,* 240:1038-1040 (1988); Huston et al., *Methods in Enzymology,* 203:46-88 (1991); Shu et al., *PNAS,* 90:7995-7999 (1993).

Changes may be made to the residues that comprise the CDRs without interfering with the ability of the antibody to recognize and bind its cognate epitope. For example, changes that do not affect epitope recognition, yet increase the binding affinity of the antibody for the epitope may be made. Several studies have surveyed the effects of introducing one or more amino acid changes at various positions in the sequence of an antibody, based on the knowledge of the primary antibody sequence, on its properties such as binding and level of expression (Yang et al., *J Mol Biol.* 254[3]: 392-403 (1995); Vaughan et al., *Nat Biotechnol.* 16[6]: 535-539 (1998); Rader et al., *Proc Natl Acad Sci U.S.A.* 95[15]:8910-8915 (1998)). In these studies (so called affinity maturation techniques), altered versions of the antibody have been generated by changing the sequences of the encoding genes in the CDR1, CDR2, CDR3, or framework regions, using methods such as oligonucleotide-mediated site-directed mutagenesis, cassette mutagenesis, error-prone PCR, DNA shuffling, or mutator-strains of *E. coli* (Vaughan et al., *Nat Biotechnol.* 16[6]:535-539 (1998)). These methods of changing the sequence of the antibody have resulted in improved affinities of the resulting antibodies (Gram et al., *Proc Natl Acad Sci U.S.A.* 89[8]:3576-3580 (1992); Davies and Riechmann, *Immunotechnology,* 2[3]:169-179 (1996); Thompson et al., *J Mol Biol.* 256[1]:77-88 (1996); Boder et al., *Proc Natl Acad Sci U.S.A.* 97[20]:10701-10705 (2000); Furukawa et al., *J Biol Chem.* 276[29]:27622-27628 (2001); Short et al., *J Biol Chem.,* 277[19]:16365-16370 (2002)).

In a preferred embodiment of the invention, the antibody of the invention is monoclonal. The term "monoclonal antibody" is well recognized in the art and refers to an antibody or a homogenous population of antibodies that is derived from a single clone. Individual antibodies from a monoclonal antibody population are essentially identical, in that minor naturally occurring mutations may be present. Antibodies from a monoclonal antibody population show a homogenous binding specificity and affinity for a particular epitope.

As used herein, "percentage identity" or "% identity" between two or more amino acid sequences or two or more nucleotide sequences refers to the ratio, expressed in %, of: the number of amino acids or nucleotides in an optimal alignment of the amino acid sequences or nucleotide sequences that are identical in both sequences (i.e. match), to the length of the alignment, i.e. the number of aligned positions, including gaps if any.

As used herein, "cell line" is to be understood a homogenous population of eukaryotic cells which is genetically stable and can be cultured. Preferably, the cell line is of animal origin. More preferably, the cell line is immortalized. Alternatively, the cell line is of plant or fungal origin. In one embodiment, the cell line of the invention is obtained by genetic transformation with a nucleic acid comprising a polynucleotide encoding the antibody or antibody fragment of the invention under suitable transcriptional and translational control elements, which are known to those skilled in the art, to allow efficient production of the antibody or antibody fragment. In another embodiment, the cell line is a hybridoma cell line LRD-915092 deposited under the Budapest Treaty at the Belgian Coordinated Collections of Microorganisms BCCM™/LMBP Collection under No. LMBP11316CB.

The term "nucleic acid" is intended to include DNA molecules and RNA molecules. A nucleic acid can be single-stranded or double-stranded.

The nucleic acids of the invention are present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. see, e.g., Sambrook, Tijssen and Ausubel. The nucleic acid sequences of the invention and other nucleic acids used to practice this invention, whether RNA, cDNA, genomic DNA, or hybrids thereof, may be isolated from a variety of sources, genetically engineered, amplified, and/or expressed recombinantly. Any recombinant expression system can be used, including, in addition to bacterial, e.g., yeast, insect or mammalian systems. Alternatively, these nucleic acids can be chemically synthesized in vitro. Techniques for the manipulation of nucleic acids, such as, e.g., subcloning into expression vectors, labeling probes, sequencing, and hybridization are well described in the scientific and patent literature, see, e.g., Sambrook, Tijssen and Ausubel. Nucleic acids can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, such as fluid or gel precipitation reactions, immunodiffusion (single or double), immunoelectrophoresis, radioimmunoassays (RIAs), enzyme-linked immunosorbent assays (ELISAs), immunofluorescent assays, Southern analysis, Northern analysis, dot-blot analysis, gel electrophoresis (e.g., SDS-PAGE), RT-PCR, quantitative PCR, other nucleic acid or target or signal amplification methods, radiolabeling, scintillation counting, and affinity chromatography.

The nucleic acid compositions of the present invention, while often in a native sequence (except for modified restriction sites and the like), from either cDNA, genomic or mixtures may be mutated, thereof in accordance with standard techniques to provide gene sequences. For coding sequences, these mutations, may affect amino acid sequence as desired. In particular, DNA sequences substantially homologous to or derived from such sequences described herein are contemplated (where "derived" indicates that a sequence is identical or modified from another sequence).

The present invention presents an isolated ADAMTS13 antibody, antibody-like scaffold or antibody fragment.

In an embodiment, said isolated antibody, antibody-like scaffold or antibody fragment comprises at least one heavy chain variable region comprising in a CDR1 region an amino acid sequence which has at least 80%, preferably 90%, or more preferably 95% identity to SEQ ID NO: 12, in a CDR2 region an amino acid sequence which has at least 80%, preferably 90%, or more preferably 95% identity to SEQ ID NO: 13 and in a CDR3 region an amino acid sequence which has at least 80%, preferably 90%, or more preferably 95% identity to SEQ ID NO: 14. In another preferred embodiment, said isolated ADAMTS13 antibody, antibody-like scaffold or antibody fragment further comprises a light chain variable region comprising in a CDR1 region an amino acid sequence which has at least 80%, preferably 90%, or more preferably 95% identity to SEQ ID NO: 17, in a CDR2 region an amino acid sequence which has at least 80% preferably 90%, or more preferably 95% identity to SEQ ID NO: 18 and in a CDR:3 region an amino acid sequence which has at least 80%, preferably 90%, or more preferably 95% identity to SEQ ID NO: 19.

In another embodiment, the said isolated antibody, antibody-like scaffold or antibody fragment comprises a heavy chain variable region with a CDR1 region consisting of SEQ ID NO: 12, a CDR2 with SEQ ID NO: 13, and a CDR3 region consisting of SEQ ID NO: 14, comprises a light chain variable region with a CDR1 region consisting of SEQ ID NO: 17, a CDR2 with SEQ ID NO: 18, and a CDR3 region consisting of SEQ ID NO: 19.

The present invention presents an isolated nucleic acid comprising a polynucleotide encoding an isolated ADAMTS13 antibody, antibody-like fragments or antibody fragment. In a preferred embodiment, said polynucleotide comprises a nucleotide sequence selected from the group consisting of SEQ ID NO: 10 and SEQ ID NO: 15.

Other embodiments refer to modified version of SEQ ID NO: 10 and 15 which do not change the encoded amino acid sequence as defined in respectively SEQ ID NO: 11 and SEQ ID NO: 16.

In a preferred embodiment, said isolated antibody, antibody-like scaffold or antibody fragment comprises at least one heavy chain variable domain having an amino acid sequence which has at least 80%, preferably 90%, or more preferably 95% identity to amino acid sequence SEQ ID NO: 11 and at least one light chain variable domain having an amino acid sequence which has at least 80%, preferably 90%, or more preferably 95% identity to amino acid sequence SEQ ID NO: 16.

In another embodiment said isolated antibody, antibody-like scaffold or antibody fragment comprises a heavy chain variable domain having an amino acid sequence which has at least 80%, preferably 90%, or more preferably 95% identity to amino acid sequence SEQ ID NO: 11, wherein the CDR regions with SEQ ID NO: 12, 13 and 14 are unmodified, and comprises a light chain variable domain having an amino acid sequence which has at least 80%, preferably 90%, or more preferably 95% identity to amino acid sequence SEQ ID NO: 16, wherein the CDR regions with SEQ ID NO: 17, 18 and 19 are unmodified. This embodiment thus envisages compounds wherein the CDRs are conserved but wherein a certain degree of variation is allowed in the variable domains outside the CDR regions.

In another preferred embodiment of the present invention said isolated ADAMTS13 antibody, antibody-like scaffold or antibody fragment comprises at least one heavy chain variable domain comprising an amino acid sequence as set out in SEQ ID NO: 11 and at least one light chain variable domain comprising an amino acid sequence as set out in SEQ ID NO: 16.

In another preferred embodiment of the present invention said isolated ADAMTS13 antibody, antibody-like scaffold or antibody fragment, comprises a heavy chain variable region comprising in a CDR1 region an amino acid sequence as set out in SEQ ID NO: 12, in a CDR2 region an amino acid sequence as set out in SEQ ID NO: 13 and in a CDR3 region an amino acid sequence as set out in SEQ ID NO: 14; and a light chain variable region comprising in a CDR1 region an amino acid sequence as set out in SEQ ID NO: 17, in a CDR2 region an amino acid sequence as set out in SEQ ID NO: 18 and in a CDR3 region an amino acid sequence as set out in SEQ ID NO: 19.

The present invention presents an isolated ADAMTS13 antibody, antibody-like scaffold or antibody fragment.

In an embodiment, said isolated antibody, antibody-like scaffold or antibody fragment comprises at least one heavy chain variable region comprising in a CDR1 region an amino acid sequence which has at least 80%, preferably 90%, or more preferably 95% identity to SEQ ID NO: 3, in a CDR2 region an amino acid sequence which has at least 80%, preferably 90%, or more preferably 95% identity to SEQ ID NO: 4 and in a CDR3 region an amino acid sequence which has at least 80%, preferably 90%, or more preferably 95% identity to SEQ ID NO: 5. In another preferred embodiment, said isolated ADAMTS13 antibody, antibody-like scaffold or antibody fragment further comprises a light chain variable region comprising in a CDR1 region an amino acid sequence which has at least 80%, preferably 90%, or more preferably 95% identity to SEQ ID NO: 8, in a CDR2 region an amino acid sequence which has at least 80% preferably 90%, or more preferably 95% identity to the sequence YAS and in a CDR:3 region an amino acid sequence which has at least 80%, preferably 90%, or more preferably 95% identity to SEQ ID NO: 9.

In another embodiment, the said isolated antibody, antibody-like scaffold or antibody fragment comprises a heavy chain variable region with a CDR1 region consisting of SEQ ID NO: 3, a CDR2 with SEQ ID NO: 4, and a CDR3 region consisting of SEQ ID NO: 5, comprises a light chain variable region with a CDR1 region consisting of SEQ ID NO: 8, a CDR2 with the sequence YAS, and a CDR3 region consisting of SEQ ID NO: 9.

In a preferred embodiment, said isolated antibody, antibody-like scaffold or antibody fragment comprises at least one heavy chain variable domain having an amino acid sequence which has at least 80%, preferably 90%, or more preferably 95% identity to amino acid sequence SEQ ID NO: 2 and at least one light chain variable domain having an amino acid sequence which has at least 80%, preferably 90%, or more preferably 95% identity to amino acid sequence SEQ ID NO: 7.

In another embodiment said isolated antibody, antibody-like scaffold or antibody fragment comprises a heavy chain variable domain having an amino acid sequence which has at least 80%, preferably 90%, or more preferably 95% identity to amino acid sequence SEQ ID NO: 2, wherein the CDR regions with SEQ ID NO: 3, 4 and 5 are unmodified, and comprises a light chain variable domain having an amino acid sequence which has at least 80%, preferably 90%, or more preferably 95% identity to amino acid sequence SEQ ID NO: 7, wherein the CDR regions with SEQ ID NO: 8, the sequence YAS and SEQ ID NO: 9 are unmodified. This embodiment thus envisages compounds wherein the CDRs are conserved but wherein a certain degree of variation is allowed in the variable domains outside the CDR regions.

In another preferred embodiment of the present invention said isolated ADAMTS13 antibody, antibody-like scaffold or antibody fragment comprises at least one heavy chain variable domain comprising an amino acid sequence as set out in SEQ ID NO: 2 and at least one light chain variable domain comprising an amino acid sequence as set out in SEQ ID NO: 7.

In another preferred embodiment of the present invention said isolated ADAMTS13 antibody, antibody-like scaffold or antibody fragment, comprises a heavy chain variable region comprising in a CDR1 region an amino acid sequence as set out in SEQ ID NO: 3, in a CDR2 region an amino acid sequence as set out in SEQ ID NO: 4 and in a CDR3 region an amino acid sequence as set out in SEQ ID NO: 5; and a light chain variable region comprising in a CDR1 region an amino acid sequence as set out in SEQ ID NO: 8, in a CDR2 region the amino acid sequence YAS and in a CDR3 region an amino acid sequence as set out in SEQ ID NO: 9.

In another preferred embodiment of the present invention said isolated ADAMTS13 antibody, antibody-like scaffold or antibody fragment is a monoclonal antibody, or a mouse monoclonal IgG1 subtype, or a humanized antibody or fragment thereof for instance a single-chain antibody, Fv fragment, a Fab fragment (e.g. Fab' fragment or a F(ab') 2 fragment) or a single domain antibodies, or a human antibody or fragment thereof. Preferably, said antibody is a monoclonal antibody. More preferably, said antibody is a humanized antibody or fragment thereof.

In a preferred embodiment, the antibody of the invention is secreted by the hybridoma cell line deposited under the Budapest Treaty at the Belgian Coordinated Collections of Microorganisms BCCM™/LMBP Collection under No. LMBP 11316CB. This hybridoma cell line will hereinafter be referred to as LRD-915092 and the secreted monoclonal antibody will hereinafter be referred to as Ab11316CB. The term "hybridoma" is well recognized in the art and refers to a cell line resulting from the fusion of a single antibody-producing cell clone and an immortal cell or tumor cell. In another preferred embodiment, the antibody of the invention is a humanized antibody of the antibody secreted by the hybridoma cell line deposited under the Budapest Treaty at the Belgian Coordinated Collections of Microorganisms BCCM™/LMBP Collection under No. LMBP 11316CB. In another preferred embodiment, the antibody of the invention is a humanized antibody comprising the CDRs of the antibody secreted by the hybridoma cell line deposited under the Budapest Treaty at the Belgian Coordinated Collections of Microorganisms BCCM™/LMBP Collection under No. LMBP 11316CB.

In a preferred embodiment, said isolated ADAMTS13 antibody, antibody-like scaffold or antibody fragment of the present invention is for use in the treatment of a haemorrhagic complication or bleeding disorder in a subject carrying an implanted circulatory assist device. Typically, said haemorraghic complication or bleeding disorder is due to said implanted circulatory assist device. Preferably said subject is a mammal, more preferably said subject is a human. Preferably, said circulatory assist device is a ventricular assist device. More preferably, said circulatory assist device is a left ventricular assist device (LVAD).

The present invention presents an isolated nucleic acid comprising a polynucleotide encoding an isolated ADAMTS13 antibody, antibody-like fragments or antibody fragment. In a preferred embodiment, said polynucleotide comprises a nucleotide sequence selected from the group consisting of SEQ ID NO: 1 and SEQ ID NO: 6.

Other embodiments refer to modified version of SEQ ID NO: 1 and 6 which do not change the encoded amino acid sequence as defined in respectively SEQ ID NO: 2 and SEQ ID NO:7.

The present invention presents an isolated cell line producing the antibody or antibody fragments of the present invention. In one embodiment, the cell line of the invention is obtained by genetic transformation with a nucleic acid comprising a polynucleotide encoding the antibody or antibody fragment of the invention under suitable transcriptional and translational control elements, which are known to those skilled in the art, to allow efficient production of the antibody or antibody fragment. In another embodiment, the cell line is a hybridoma cell line LRD-915092 deposited under the Budapest Treaty at the Belgian Coordinated Collections of Microorganisms BCCM™/LMBP Collection under No. LMBP 11316CB.

The present invention also provides a pharmaceutical composition comprising said ADAMTS13 antibody, antibody-like fragment or antibody fragment, for use in the prevention or treatment of a haemorrhagic complication or bleeding disorder in a subject carrying an implanted circulatory assist device. Typically, said haemorrhagic complication or bleeding disorder is due to said implanted circulatory assist device. Preferably, said subject is a mammal, more preferably, said subject is a human. Preferably, said circulatory assist device is a ventricular assist device. More preferably, said circulatory assist device is a left ventricular assist device.

The present invention also provides a method of treatment or prevention of a haemorrhagic complication or bleeding disorder in a subject carrying an implanted circulatory assist device, comprising administering to said subject said ADAMTS13 antibody, antibody-like scaffold or antibody fragment. Typically, said haemorrhagic complication or bleeding disorder is due to said implanted circulatory assist device. Preferably, said subject is a mammal, more preferably said subject is a human. Preferably, said circulatory assist device is a ventricular assist device. More preferably, said circulatory assist device is a left ventricular assist device.

The present invention presents a molecule that is an antibody, antibody-like scaffold or antibody fragment that binds ADAMTS13 for use in the treatment or prevention of a haemorrhagic complication or bleeding disorder in a subject carrying an implanted circulatory assist device. Typically, said haemorrhagic complication or bleeding disorder is due to said implanted circulatory assist device. Preferably, said circulatory assist device is a ventricular assist device. More preferably, said circulatory assist device is a left ventricular assist device.

The present invention presents a molecule that is an antigen binding protein comprising at least one first immunoglobulin variable domain capable of binding to human ADAMTS13 for use in the treatment or prevention of a haemorrhagic complication or bleeding disorder in a subject carrying an implanted circulatory assist device. Typically, said haemorraghic complication or bleeding disorder is due to said implanted circulatory assist device. Preferably, said circulatory assist device is a ventricular assist device. More preferably, said circulatory assist device is a left ventricular assist device.

In a preferred embodiment, said molecule is an ADAMTS13 binding molecule and an ADAMTS13 inhibitor. In another preferred embodiment, said ADAMTS13 binding or inhibiting molecule is selected from the group consisting of a specific polyclonal antibody, a monoclonal antibody, a full-length antibody, a binding fragment of an antibody and a surrogate of an antibody. In another preferred embodiment, said ADAMTS13 binding or inhibiting molecule is selected from the group consisting of a Fab', F(ab')2, Fab, Fv, vIgG, scFv fragments and surrobodies, rIgG, disulfide-stabilized Fv antibodies (dsFv), diabodies, triabodies, and single domain antibodies, such as a camelized antibody or nanobody or humanized camel or shark antibody or nanobody and capable of binding to human ADAMTS13. In another preferred embodiment, ADAMTS13 binding or inhibiting molecule is an ADAMTS13 antigen-binding fragment of a monoclonal antibody of the group consisting of a scFV, Fab, Fab2, F(ab')2, Fv or dAb and capable of binding to human ADAMTS13.

In another preferred embodiment, said molecule is an ADAMTS13 binding or inhibiting molecule, which is a chimeric or humanized antibody or antigen-binding fragment thereof and capable of binding to human ADAMTS13. Preferably, said ADAMTS13 binding or inhibiting molecule specifically binds to ADAMTS13. More preferably, said ADAMTS13 binding or inhibiting molecule specifically binds to human ADAMTS13.

A specific embodiment relates to a monoclonal antibody comprising six CDRs wherein CDRH1 is NYAMS (SEQ ID NO: 12), CDRH2 is TITTGGFYTFYSDSVKG (SEQ ID NO: 13), and CDRH3 is HRYDDYYALDY (SEQ ID NO: 14) and CDRL1 is NVSSSVSYMR (SEQ ID NO:17), CDRL2 DTSKLAS is (SEQ ID NO: 18) and CDRL3 FQGNGYPLT is (SEQ ID NO:19).

Another specific embodiment refers to a monoclonal antibody with a variable heavy chain having 80%, 85%, 90%, 95%, 99%, or 100% sequence identity with the amino acids sequence as defined in SEQ ID NO:11, and comprising the above CDRs with SEQ ID NO: 12-14, and with a variable light chain having 80%, 85%, 90%, 95%, 99%, or 100% sequence identity with the amino acids sequence as defined in SEQ ID NO:16 and comprising the above CDRs with SEQ ID NO: 17-19.

Another specific embodiment relates to a monoclonal antibody comprising six CDRs wherein CDRH1 is GFTFSSYG (SEQ ID NO: 3), CDRH2 is ISSGGTYT (SEQ ID NO: 4), and CDRH3 is AARVAWDFGSTYDYAMDY (SEQ ID NO: 5) and CDRL1 is QSLSNY (SEQ ID NO:8), CDRL2 is YAS and CDRL3 is QQSNSWPLT (SEQ ID NO:9).

Another specific embodiment refers to a monoclonal antibody with a variable heavy chain having 80%, 85%, 90%, 95%, 99%, or 100% sequence identity with the amino acids sequence as defined in SEQ ID NO:2 and a variable light chain having 80%, 85%, 90%, 95%, 99%, or 100% sequence identity with the amino acids sequence as defined in SEQ ID NO:7 and comprising the above six CDRs with SEQ ID NO: 3-5 and SEQ ID NO: 8, the sequence YAS and SEQ ID NO: 9.

In a specific embodiment, the variable heavy chain is defined by a shorter partial sequence as defined by the amino acid sequence of SEQ ID NO: 21 or the corresponding DNA sequence of SEQ ID NO: 20. Based on these sequences primers can be generated to re-sequence the N-terminal part. Thus a specific embodiment describes a variable heavy chain obtainable by extending the sequence of SEQ ID NO:21 or 22.

In another preferred embodiment, said molecule is a humanized antibody of the antibody produced by a hybridoma deposited under the Budapest Treaty at the Belgian Coordinated Collections of Microorganisms BCCM™/LMBP Collection under No. LMBP 11316CB.

In another preferred embodiment, said molecule is a humanized antibody comprising CDRs of the antibody produced by a hybridoma deposited under the Budapest Treaty at the Belgian Coordinated Collections of Microorganisms BCCM™/LMBP Collection under No. LMBP 11316CB.

In a preferred embodiment, said ADAMTS13 binding molecule comprises an antibody, or antigen-binding fragment thereof, that binds to ADAMTS13 with a dissociation constant (K D) of 50 nM or less, 20 nM or less, 5 nM or less, 1 nM or less, 500 pM or less, 150 pM or less, 150 pM or less, 125 pM or less, 100 pM or less as determined by real-time biospecific interaction analysis (BIA) using surface plasmon resonance (SPR) technology, or with an IC50 of 50 nM or less, 20 nM or less, 5 nM or less, 1 nM or less, 500 pM or less, 100 pM or less, 75 pM or less, 50 pM or less.

In another preferred embodiment, said ADAMTS13 binding molecule comprises an antibody, or antigen binding fragment thereof, that binds to a neutralizing epitope of human ADAMTS13 with an affinity of at least about $5 \times 10^4$ liter/mole as measured by an association constant (Ka), or of at least $5 \times 10^5$ liter/mole, or of at least $5 \times 10^6$ liter/mole, or of at least $1 \times 10^7$ liter/mole, or of at least $1 \times 10^7$ liter/mole.

In another preferred embodiment, said ADAMTS13 inhibitor further comprises a component selected from the group consisting of pharmaceutically acceptable carriers, diluents and excipients.

In another preferred embodiment, said circulatory assist device implanted in said subject is a ventricular assist device (VAD). In an even more preferred embodiment, said circulatory assist device implanted in said subject is a left ventricular assist device (LVAD).

EXAMPLES

Material and Methods

DNA and Amino Acid Sequencing of the Variable Domains of Anti-ADAMTS13 Monoclonal Antibody Ab11316CB.

Total RNA was isolated from 1×10⁶ hybridoma cells expressing mAb Ab11316CB using the QIAamp RNA blood mini kit (Qiagen, Venlo, The Netherlands). The quality and concentration of the RNA was determined by spectrophotometry. Full length cDNA was produced with an oligo(dT) 20 primer according to the Thermoscript™ RT-PCR system (Invitrogen, Carlsbad, Calif.). The DNA coding for the variable domain of the heavy (VH) and the light chain (VL) were amplified separately using 2 µl cDNA, 1.5 mM MgCl2, 0.2 mM dNTP, 5U Platinum® Taq DNA polymerase, 0.2 µM backward primer (hybridising in FR1) and 0.2 µM forward primer (hybridizing in FR4). Amplification was performed in a thermocycler for 3 min at 92° C. and 30 cycles of 1 min at 92° C., 1 min at 56° C., 2 min at 72° C., followed by a final elongation step for 10 min at 72° C. PCR fragments were purified (Nucleospin, Macherey-Nagel) and the sequence was determined by DNA sequencing (GATC Biotech, AG, Konstanz, Germany).

This antibody Ab11316CB, is defined by CDRs GFTFSSYG [SEQ ID NO: 3], ISSGGTYT [SEQ ID NO: 4], ARRVAWDFGSTYDYAMDY [SEQ ID NO: 5], QSLSNY [SEQ ID NO: 8], YAS, and QQSNSWPLT [SEQ ID NO:9] and comprising the amino acid sequence of SEQ ID NO: 2 and SEQ ID NO:7 (corresponding DNA sequences are shown in SEQ ID NO: 1 and 6). The antibody is secreted by hybridoma cell line LRD-915092 deposited under the Budapest Treaty at the Belgian Coordinated Collections of Microorganisms BCCM™/LMBP Collection [Ghent University—Department of Biomedical Molecular Biology, Technologiepark 927, 9052 Gent Zwijnaarde] under No. LMBP 11316CB on Sep. 16, 2015.

The antibody is also called 3H9.

DNA and Amino Acid Sequencing of the Variable Domains of Anti-ADAMTS13 Monoclonal Antibody 17C7.

Total RNA was isolated from 1×10⁶ hybridoma cells expressing mAb 17C7 using the QIAamp RNA blood mini kit (Qiagen, Venlo, The Netherlands). The quality and concentration of the RNA was determined by spectrophotometry. Full length cDNA was produced with an oligo(dT)20 primer according to the Thermoscript™ RT-PCR system (Invitrogen, Carlsbad, Calif.). The DNA coding for the variable domain of the heavy (VH) and the light chain (VL) were amplified separately using 2 µl cDNA, 1.5 mM MgCl2, 0.2 mM dNTP, 5U Platinum® Taq DNA polymerase, 0.2 µM backward primer (hybridising in FR1) and 0.2 µM forward primer (hybridizing in FR4). Amplification was performed in a thermocycler for 3 min at 92° C. and 30 cycles of 1 min at 92° C., 1 min at 56° C., 2 min at 72° C., followed by a final elongation step for 10 min at 72° C. PCR fragments were purified (Nucleospin, Macherey-Nagel) and the sequence was determined by DNA sequencing (GATC Biotech, AG, Konstanz, Germany).

This antibody Ab11316CB (also referred to as 3H9), is defined by CDRs NYAMS [SEQ ID NO:12], TITTGGFYTFYSDSVKG [SEQ ID NO:13], HRYDDYYALDY [SEQ ID NO:14], NVSSSVSYMR [SEQ ID NO:17], DTSKLAS [SEQ ID NO:18], and FQGNGYPLT [SEQ ID NO:19] and comprises the amino acid sequence of SEQ ID NO: 11 and SEQ ID NO:16 (corresponding DNA sequences are shown in SEQ ID NO: 10 and 15). This antibody is secreted by hybridoma cell line LRD-915092 deposited under the Budapest Treaty at the Belgian Coordinated Collections of Microorganisms BCCM™/LMBP Collection under No. LMBP 11316CB on Sep. 15, 2015.

EXAMPLES

Example 1. Cross Reactivity of the Anti-ADAMTS13 Monoclonal Antibody Ab11316CB with ADAMTS13 of Sheep and Pigs The ADAMTS13 activity in plasma was determined with the use of a FRETS-VWF73 assay (Kokame et al., *Br J Haematol.*, 129: 93-100 (2005)). The activity of ADAMTS13 in sheep plasma (SP) was compared with the activity in normal human plasma (NHP) and pig serum. Next, also the antibody Ab11316CB (100 µg/ml) was added. The activity of ADAMTS13 in different plasmas and sera was determined via NHP, in which the activity was set at 100%.

The anti-ADAMTS13 antibody Ab11316CB is capable of inhibiting the activity of ADAMTS13 present in NHP and pig serum, but Ab11316CB cannot inhibit the activity of ADAMTS13 in sheep plasma. As a control inhibitor EDTA (a chelator of $Zn^{2+}$ and $Ca^{2+}$, which are necessary for the activity of ADAMTS13) was added, which could inhibit the ADAMTS13 activity in sheep plasma (FIG. 5).

Example 2. Blocking ADAMTS13 Activity Protects Against Loss of HMW VWF Multimers in an In Vitro LVAD System The inhibiting anti-ADAMTS13 antibody Ab11316CB is used to block ADAMTS13 activity. The non-functional anti-ADAMTS13 antibody 5C11 was used as a control. Different doses (1 µg/ml, 4 µg/ml and 20 µg/ml) of the antibody Ab11316CB (inhibiting ADAMTS13 activity) or 5C11 (negative control antibody with no functional effect on ADAMTS13) were added to full blood and used in an in vitro LVAD pump. Blood samples were taken before (TO) and after 5, 30 and 180 minutes to determine the multimer distribution. The plasma samples were loaded on a 0.8% stacking and 1.2% running agarosegel. After running the gel, the gel was dried and incubated with an alkaline phosphatase labelled anti-human VWF antibody. Next, a colour reaction was performed to visualize the multimer pattern (FIG. 6).

To calculate the percentage of the low molecular weight (LMW) VWF, middle molecular weight (MMW) VWF and high molecular weight (HMW) VWF multimers, densitometric analysis was performed using ImageJ software (version 1.47, National Institute of Health, Bethesda, USA). For each lane, the complete multimer was selected and the density was graphed. The lowest 5 (1-5 mer), the intermediate (6-10 mer), and the high molecular weight (HMW; >10 mer) multimers were selected and the density of the HMW multimers relative to the complete multimer was calculated as a percentage.

Figure 7:
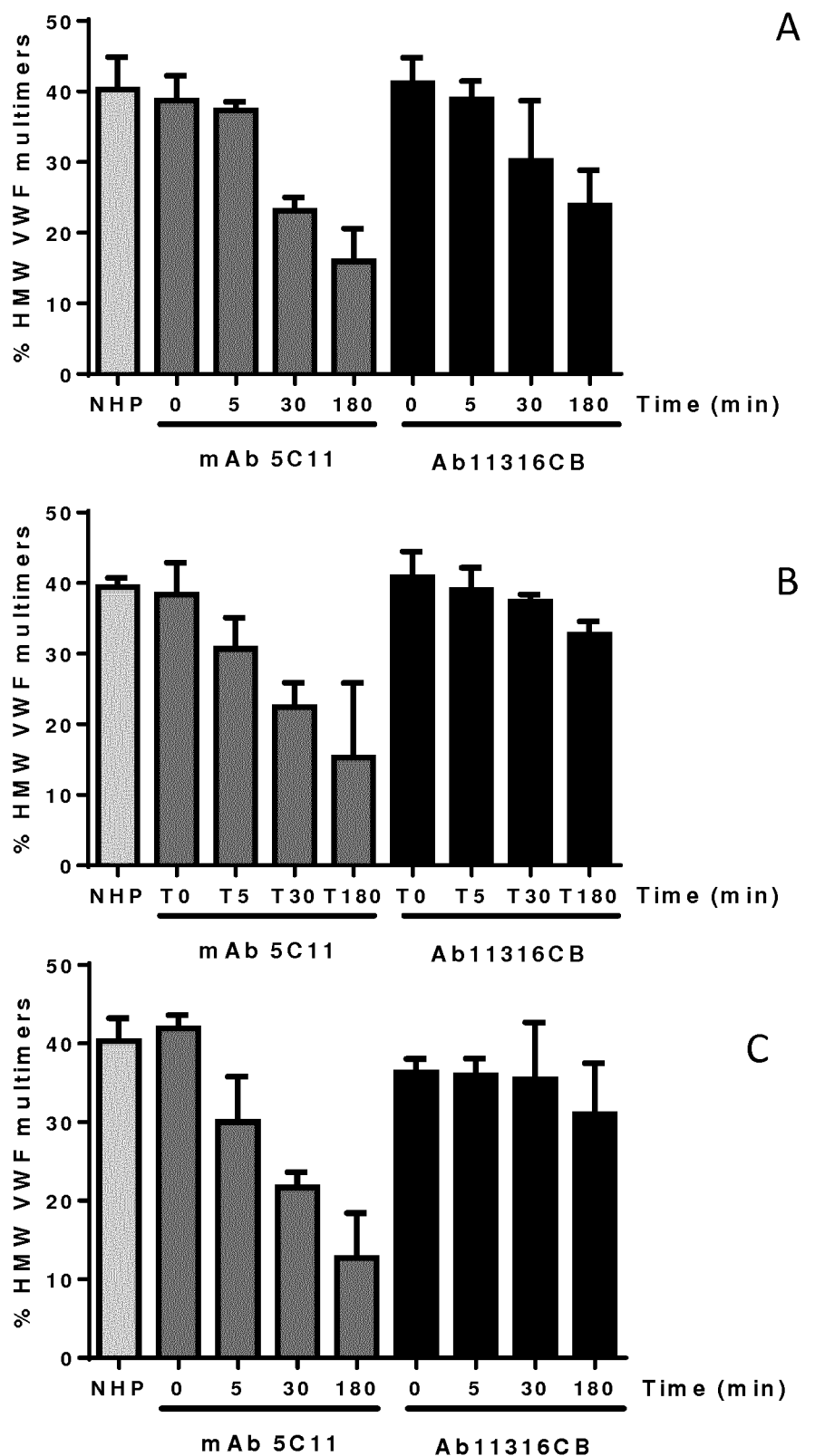

In vitro LVAD experiments were performed in triplicate with different doses (1 µg/ml, 4 µg/ml and 20 µg/ml) of the inhibiting anti-ADAMTS13 antibody Ab11316CB or the control anti-ADAMTS13 antibody 5C11. Percentage of LMW, MMW and HMW VWF multimers were calculated and mean data are presented in FIG. 7. Interestingly, the inhibiting anti-ADAMTS13 antibody Ab11316CB dose dependently protects VWF from loss of its HMW multimers while the control antibody has no effect. Maximal inhibition of VWF multimer proteolysis is obtained with 20 µg/ml Ab11316CB (FIG. 7C).

Example 3: Characterization of 17C7 and Human Plasma

Monoclonal Anti-ADAMTS13 Antibody 17C7 Captures Human ADAMTS13 from Human Plasma.

A 96-well plate was coated with 17C7 or 3H9 (Ab11316CB) (5 µg/mL), blocked and a serial dilution of normal human plasma (NHP) or plasma of a congenital TTP patient was added (15% in first well, 1.5/2.5 dilution). Bound ADAMTS13 was detected with in house developed biotinylated monoclonal anti-ADAMTS13 antibodies 17G2 and 19H4 (1.5 µg/mL) followed by addition of streptavidin labelled with horse radish peroxidase (HRP). Colouring reaction was performed with orthophenylene diamine (OPD) and $H_2O_2$. The reaction was stopped with H2SO4. Data are represented as mean+/−SD, n=3.

When coating a constant concentration of 17C7 or 3H9 (Ab11316CB) and adding a dilution series of normal human plasma, both monoclonal anti-ADAMTS13 antibodies 17C7 and 3H9 (Ab11316CB) efficiently capture human ADAMTS13 from human plasma (FIG. 8).

Monoclonal Anti-ADAMTS13 Antibody 17C7 has a Higher Affinity for ADAMTS13 than Monoclonal Anti-ADAMTS13 Antibody 3H9 (Ab11316CB).

A 96-well plate was coated with a serial dilution of either 17C7 or 3H9 (Ab11316CB) (ranging from 10 µg/mL to 0.02 µg/mL), blocked and a constant amount of normal human plasma (15%) was added. Detection of bound ADAMTS13 occurred as described in 1.1. Data are represented as mean+/−SD, n=3. Lines were fitted by nonlinear regression. When coating a dilution series of 17C7 or 3H9 and adding a constant amount of normal human plasma, half maximal binding (Ka) of human ADAMTS13 was observed at 0.51 µg/mL for 17C7 and 1.5 µg/mL for 3H9 (Ab11316CB) showing that 17C7 has a higher affinity for ADAMTS13 in human plasma than 3H9 (Ab11316CB) (FIG. 9).

Monoclonal Biotinylated Anti-ADAMTS13 Antibody 17C7 Detects Human ADAMTS13 from Human Plasma.

A 96-well plate was coated with the anti-ADAMTS13 monoclonal antibody 4B9 (5 µg/mL), blocked and a serial dilution of normal human plasma or plasma of a congenital TTP patient was added (15% in first well, 1.5/2.5 dilution), bound ADAMTS13 was detected with biotinylated anti-ADAMTS13 monoclonal antibody 17C7 (1.5 µg/mL) followed by addition of streptavidin labelled with horse radish peroxidase (HRP). Colouring reaction was performed with orthophenylene diamine (OPD) and $H_2O_2$. The reaction was stopped with H2SO4. Data are represented as mean+/−SD, n=2. When coating a constant amount of monoclonal anti-ADAMTS13 antibody 4B9, biotinylated 17C7 efficiently detects human ADAMTS13 from normal human plasma (FIG. 10).

Monoclonal Anti-ADAMTS13 Antibody 17C7 is a More Potent Inhibitor of Human ADAMTS13 than Monoclonal Anti-ADAMTS13 Antibody 3H9 (Ab11316CB).

Normal human plasma was pre-incubated for 15 minutes with different concentrations of 17C7 or 3H9 (Ab11316CB). ADAMTS13 activity in plasma was determined using the FRETS-VWF73 assay (Kokame et al., Br J Haematol., 129: 93-100 (2005)) (FIG. 11 A and B). ADAMTS13 activity in NHP was set at 100%. Non-inhibitory anti-ADAMTS13 monoclonal antibody 15D1 was used as a control. When incubating NHP with different concentrations of anti-ADAMTS13 antibodies 17C7 or 3H9 (Ab11316CB), half maximal inhibitory concentration (IC50) was observed at 0.47 µg/mL for 17C7 and 4.43 µg/mL for 3H9 (Ab11316CB) showing that 17C7 is a more potent inhibitor of human ADAMTS13 activity than 3H9 (FIG. 12).

Example 4: Characterization of 17C7 and Ovine Plasma

Cross Reactivity of Monoclonal Anti-ADAMTS13 Antibody 17C7 with Ovine ADAMTS13.

ADAMTS13 activity in plasma was determined using the FRETS-VWF73 assay. Inhibition of ADAMTS13 in ovine plasma (OP) was studied using different anti-ADAMTS13 antibodies. The activity of ovine ADAMTS13 in ovine plasma was set at 100%. Anti-ADAMTS13 antibody 17C7 is capable of inhibiting ovine ADAMTS13, while the anti-ADAMTS13 monoclonal antibodies 3H9 (Ab11316CB) and 5C11 are not. As a control EDTA (Ethylenediaminetetraacetic acid, a chelator of $Zn^{2+}$ and $Ca^{2+}$, which are necessary for the activity of ADAMTS13) was added (FIG. 13).

Monoclonal Anti-ADAMTS13 Antibody 17C7 is a Potent Inhibitor of Ovine ADAMTS13.

Ovine plasma (OP) was pre-incubated for 15 minutes with different concentrations of 17C7. ADAMTS13 activity in plasma was determined using the FRETS-VWF71 assay (Muia, J. et al., Journal of Thrombosis and Haemostasis., 11: 1511-1518 (2013)) (FIG. 14A). ADAMTS13 activity in ovine plasma was set at 100%. When incubating ovine plasma with different concentrations of anti-ADAMTS13 antibody 17C7 half maximal inhibitory concentration (IC50) was observed at 2.4 µg/mL (FIG. 14B).

Example 5: Left Ventricular Assist Device Implantation in Sheep

VWF Multimeric Profile in Sheep Before and after Implantation of a Left Ventricular Assist Device Blood samples were taken before (Pre) and after (Post) implantation of a left ventricular assist device (Impella, Abiomed, Germany, Aachen) device in 4 sheep. The plasma samples were loaded on a 0.8% stacking and 1.2% running agarose gel. After running the gel, the gel was dried and incubated with an alkaline phosphatase labelled anti-human VWF antibody. Next, a colouring reaction was performed to visualize the VWF multimer pattern (FIG. 15A). To calculate the percentage of low molecular weight (LMW) VWF, medium molecular weight (MMW) VWF and high molecular weight (HMW) VWF multimers, densitometric analysis was performed using ImageJ software (version 1.47, National Institute of Health, Bethesda, USA). For each lane, the complete multimer was selected and the density was graphed. The lowest 5 (1-5 mer), the medium (6-10 mer), and the high molecular weight (HMW; >10 mer) multimers were selected and the density of the HMW multimers relative to the complete multimer was calculated as a percentage. Mean data of the LMW, MMW and HMW VWF multimers are presented in FIG. 15B. For 3 of the 4 sheep, HMW VWF multimers decreased after Impella implantation.

Collagen Binding and Ristocetin Cofactor Activity of Ovine VWF Before and after Implantation of a Left Ventricular Assist Device.

Binding of VWF to its ligands collagen and platelet glycoprotein (GP) Ib was determined via ELISA. To determine the collagen binding activity (VWF:CB), 25 µg/mL of human collagen type III was coated on a 96-well ELISA plate, ovine plasma was added and bound VWF was detected with polyclonal anti-human VWF antibodies labelled with horse radish peroxidase (HRP). Colouring reaction was performed with orthophenylene diamine (OPD) and $H_2O_2$. The reaction was stopped with H2SO4. To measure the VWF ristocetin cofactor activity (VWF:RCo) (Vanhoorelbeke et al., Thrombosis and haemostasis, 83: 107-113 (2000)), 5 μg/mL of anti-GPIb monoclonal antibody 2D4 was coated on a 96-well ELISA plate and a recombinant fragment of GPIb was captured. Next, ovine plasma containing VWF was added in the presence of ristocetin, which allows binding of VWF to GPIb under static conditions, and bound VWF was detected with anti-VWF antibodies labelled with HRP. Colouring reaction was performed with orthophenymene diamine (OPD) and $H_2O_2$. The reaction was stopped with H2SO4. Ovine plasma before implantation of the left ventricular assist device was used as a reference and the activity was set at 100%. Next the ratio of VWF:CB over VWF antigen (VWF:Ag) (VWF:CB/VWF:Ag) (FIG. 16A) or VWF:RCo over VWF:Ag (VWF:RCo/VWF:Ag) (FIG. 16B) was calculated. As expected, the mean VWF:CB/VWF:Ag ratio was significantly decreased after implantation of the left ventricular assist device but this was not the case for the VWF:RCo/VWF:Ag ratio.

Example 6: Monoclonal Anti-ADAMTS13 Antibody 17C7 Injection in a Naïve Sheep

In Vivo Inhibition of Sheep ADAMTS13.

A dose of 600 μg/kg monoclonal anti-ADAMTS13 antibody 17C7 was injected in one sheep every 48 hours. Blood samples were collected before and 2 minutes after each injection of 17C7 (red arrows). In addition, blood samples were collected every 24 hours. ADAMTS13 activity in plasma was determined using the FRETS-VWF71 assay (FIG. 14). ADAMTS13 activity at baseline levels (0 hours) was set as 100%. Ovine ADAMTS13 activity was fully inhibited until 14 days after the first injection (FIG. 17).

Antibody Levels in Plasma in a Sheep Injected with Monoclonal Anti-ADAMTS13 Antibody 17C7.

A 96-well ELISA plate was coated with 5 μg/mL goat anti-mouse (GAM) IgG Fab specific antibodies, ovine plasma was added and bound monoclonal anti-ADAMTS13 antibody 17C7 was detected with GAM antibodies labelled with horse radish peroxidase (HRP). Colouring reaction was performed with orthophenylene diamine (OPD) and $H_2O_2$. The reaction was stopped with H2SO4. A dilution series of phosphate-buffered saline (PBS) spiked with a known concentration of 17C7 was used as a calibration curve to calculate the plasma levels of 17C7. Injection of 17C7 in the sheep resulted in a mean initial plasma concentration of 20 μg/mL and then declined after 14 days to 10 μg/mL (FIG. 18).

VWF Antigen Levels and VWF Collagen Binding Activity in Plasma of a Sheep Injected with Monoclonal Anti-ADAMTS13 Antibody 17C7.

A 96-well ELISA plate was coated with anti-human VWF antibodies (1/1000 dilution), ovine plasma (OP) was added and bound VWF was detected with polyclonal anti-human VWF antibodies labelled with horse radish peroxidase (HRP). Colouring reaction was performed with orthophenylene diamine (OPD) and $H_2O_2$. The reaction was stopped with H2SO4. To measure the collagen binding activity (VWF:CB), 25 μg/mL human collagen type III was coated on a 96-well ELISA plate, ovine plasma was added and bound VWF was detected with polyclonal anti-human VWF antibodies labelled with horse radish peroxidase. Colouring reaction was performed with orthophenylene diamine (OPD) and $H_2O_2$. The reaction was stopped with H2SO4. VWF antigen levels decreased (FIG. 19A) after the injection of monoclonal antibody 17C7, but VWF:CB/VWF:Ag ratios were normal (FIG. 19B).

Hematological Parameters in a Sheep after Injection of Monoclonal Anti-ADAMTS13 Antibody 17C7.

Whole blood was collected to perform blood cell counts (platelets (FIG. 20A)), white blood cells (FIG. 20F) red blood cells (FIG. 20G), haemoglobin (FIG. 20B) and to measure lactate dehydrogenase (LDH) (FIG. 20C) (marker of tissue damage), troponnin T (FIG. 20D) (maker for heart failure) and creatinin (FIG. 20E) (marker for kidney failure) levels. Blood parameters were normal but the platelet count dropped from 96 hours until day 9 below reference values (dotted line) (FIG. 20).

The invention claimed is:

1. A method of treating a haemorrhagic complication or bleeding disorder in a subject carrying an implanted circulatory assist device, the method comprising the step of administering to said individual an antigen binding molecule specifically binding to a disintegrin and metalloproteinase with a thrombospondin type 1 motif, member 13 (ADAMTS13) and inhibiting human von Willebrand factor (VWF) cleavage by ADAMTS13, wherein said antigen binding molecule comprises:
   a variable heavy chain wherein the sequence of the CDR1, CDR2, and CDR3 regions of the variable heavy chain correspond to, respectively, SEQ ID NO: 12, SEQ ID NO: 13, and SEQ ID NO: 14; and
   a variable light chain, wherein the sequence of the CDR1, CDR2, and CDR3 regions of the variable light chain correspond to, respectively, SEQ ID NO: 17, SEQ ID NO: 18, and SEQ ID NO: 19.

2. The method according to claim 1, wherein said antigen binding molecule is an antibody, an antibody-like scaffold or an antibody fragment.

3. The method according to claim 1, wherein said antigen binding molecule is selected from the group consisting of a specific polyclonal antibody, a monoclonal antibody, a full-length antibody, a binding fragment of an antibody and a surrogate of an antibody.

4. The method according to claim 1, wherein said antigen binding molecule is selected from the group consisting of aFab', F(ab')2, Fab, Fv, vIgG, scFv fragments and surrobodies, rIgG, disulfide-stabilized Fv antibodies (dsFv), diabodies, triabodies, and single domain antibodies, such as a camelized antibody or nanobody or humanized camel or shark antibody or nanobody.

5. The method according to claim 1, wherein said antigen binding molecule is a fragment of a monoclonal antibody of the group consisting of a scFV, Fab, Fab2, F(ab')2, Fv or dAb.

6. The method according to claim 1, wherein said antigen binding molecule is a chimeric or humanized antibody or antigen-binding fragment thereof.

7. The method according to claim 3, wherein said antigen binding molecule is an antibody or antibody fragment, wherein the variable domain comprises a VH region that has outside the CDR regions at least 80% identity with the amino acid sequence of SEQ ID NO: 11 and a VL region that has outside the CDR regions at least 80% identity to the amino acid sequence of SEQ ID NO: 16.

8. The method according to claim 1, wherein said antigen binding molecule binds to ADAMTS13 with a dissociation constant (KD) of 150 pM or less, as determined by real-time biospecific interaction analysis (BIA) using surface plasmon resonance (SPR) technology, or with an IC50 of 100 pM or less.

9. The method according to claim 1, wherein said antigen binding molecule binds to a neutralizing epitope of human ADAMTS13 with an affinity of at least about $5 \times 10^4$ liter/mole as measured by an association constant (Ka).

10. The method according claim 1, whereby said circulatory assist device implanted in said subject is a ventricular assist device (VAD).

11. The method according to claim 1, whereby said circulatory assist device implanted in said subject is a left ventricular assist device (LVAD).

12. An antigen binding molecule specifically binding to a disintegrin and metalloproteinase with a thrombospondin type 1 motif, member 13 (ADAMTS13) and inhibiting ADAMTS13, which is an antibody or antibody fragment comprising:
   a variable heavy chain, wherein the sequence of the CDR1, CDR2, and CDR3 regions of the variable heavy chain correspond to, respectively, SEQ ID NO: 12, SEQ ID NO:13, and SEQ ID NO: 14; and
   a variable light chain, wherein the sequence of the CDR1, CDR2, and CDR3 regions of the variable light chain correspond to, respectively, SEQ ID NO: 17, SEQ ID NO:18, and SEQ ID NO:19.

13. The antigen binding molecule according to claim 12, wherein the variable domain comprises a VH region that has outside the CDR regions at least 80% identity to amino acid sequence SEQ ID NO:11 and comprises a VL region comprising an amino acid sequence which has outside the CDR regions at least 80% identity to amino acid sequence SEQ ID NO: 16.

14. The antigen binding molecule according to claim 12, wherein the variable domain comprises a VH region that has outside the CDR regions at least 90% identity to amino acid sequence SEQ ID NO:11 and comprises a VL region comprising an amino acid sequence which has outside the CDR regions at least 90% identity to amino acid sequence SEQ ID NO: 16.

15. The antigen binding molecule according to claim 12, wherein the variable domain comprises a VH region that has outside the CDR regions at least 95% identity to amino acid sequence SEQ ID NO:11 and comprises a VL region comprising an amino acid sequence which has outside the CDR regions at least 95% identity to amino acid sequence SEQ ID NO: 16.

* * * * *

SEQUENCE LISTING

```
<160> NUMBER OF SEQ ID NOS: 21

<210> SEQ ID NO 1
<211> LENGTH: 366
<212> TYPE: DNA
<213> ORGANISM: Mus musculus
<220> FEATURE:
<221> NAME/KEY: CDS
<222> LOCATION: (1)..(366)
<223> OTHER INFORMATION: variable heavy chain of mononoclonal
      anti-ADAMTS13 antibody 3H9

<400> SEQUENCE: 1 gag gtg cag ctg gtg gag tct ggg gga gac tta gtg aag cct gga ggg      48
Glu Val Gln Leu Val Glu Ser Gly Gly Asp Leu Val Lys Pro Gly Gly
1               5                   10                  15 tcc ctg aaa ctc tcc tgt gca gcc tct gga ttc act ttc agt agc tat      96
Ser Leu Lys Leu Ser Cys Ala Ala Ser Gly Phe Thr Phe Ser Ser Tyr
            20                  25                  30 ggc atg tct tgg gtt cgc cag act cca gac aag agg ctg gag tgg gtc     144
Gly Met Ser Trp Val Arg Gln Thr Pro Asp Lys Arg Leu Glu Trp Val
        35                  40                  45
```

```
gca acc att agt agt ggt gga act tac acc tac tat gca gac act gtg    192
Ala Thr Ile Ser Ser Gly Gly Thr Tyr Thr Tyr Tyr Ala Asp Thr Val
    50              55                  60 aag ggg cga ttc acc atc tcc aga gac aat gcc aag aac acc ctg tac    240
Lys Gly Arg Phe Thr Ile Ser Arg Asp Asn Ala Lys Asn Thr Leu Tyr
65              70                  75                  80 ctg caa atg agc agt ctg acg tct gaa gac tca gcc atg ttt tac tgt    288
Leu Gln Met Ser Ser Leu Thr Ser Glu Asp Ser Ala Met Phe Tyr Cys
                85                  90                  95 gca aga cgg gtg gct tgg gac ttc ggt agt acc tac gac tat gct atg    336
Ala Arg Arg Val Ala Trp Asp Phe Gly Ser Thr Tyr Asp Tyr Ala Met
                100                 105                 110 gac tac tgg ggc caa ggg acc acg gtc acc                            366
Asp Tyr Trp Gly Gln Gly Thr Thr Val Thr
        115                 120
```

<210> SEQ ID NO 2
<211> LENGTH: 122
<212> TYPE: PRT
<213> ORGANISM: Mus musculus

<400> SEQUENCE: 2

```
Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Trp Val
        35                  40                  45

Ala Thr Ile Ser Ser Gly Gly Thr Tyr Thr Tyr Tyr Ala Asp Thr Val
    50              55                  60

Lys Gly Arg Phe Thr Ile Ser Arg Asp Asn Ala Lys Asn Thr Leu Tyr
65              70                  75                  80

Leu Gln Met Ser Ser Leu Thr Ser Glu Asp Ser Ala Met Phe Tyr Cys
                85                  90                  95

Ala Arg Arg Val Ala Trp Asp Phe Gly Ser Thr Tyr Asp Tyr Ala Met
                100                 105                 110

Asp Tyr Trp Gly Gln Gly Thr Thr Val Thr
        115                 120
```

<210> SEQ ID NO 3
<211> LENGTH: 8
<212> TYPE: PRT
<213> ORGANISM: Artificial Sequence
<220> FEATURE:
<223> OTHER INFORMATION: 3H9 variable heavy chain CDR1

<400> SEQUENCE: 3

```
Gly Phe Thr Phe Ser Ser Tyr Gly
1               5
```

<210> SEQ ID NO 4
<211> LENGTH: 8
<212> TYPE: PRT
<213> ORGANISM: Artificial Sequence
<220> FEATURE:
<223> OTHER INFORMATION: 3H9 variable heavy chain CDR2

<400> SEQUENCE: 4

```
Ile Ser Ser Gly Gly Thr Tyr Thr
1               5
```

-continued

```
<210> SEQ ID NO 5
<211> LENGTH: 18
<212> TYPE: PRT
<213> ORGANISM: Artificial Sequence
<220> FEATURE:
<223> OTHER INFORMATION: 3H9 variable heavy chain CDR3

<400> SEQUENCE: 5

Ala Arg Arg Val Ala Trp Asp Phe Gly Ser Thr Tyr Asp Tyr Ala Met
1               5                   10                  15

Asp Tyr

<210> SEQ ID NO 6
<211> LENGTH: 312
<212> TYPE: DNA
<213> ORGANISM: Mus musculus
<220> FEATURE:
<221> NAME/KEY: CDS
<222> LOCATION: (1)..(312)
<223> OTHER INFORMATION: variable ligth chain of mononoclonal
      anti-ADAMTS13 antibody 3H9

<400> SEQUENCE: 6 gac att gag ctc acc cag tct cca gcc acc ctg tct gtg act cca gga      48
Asp Ile Glu Leu Thr Gln Ser Pro Ala Thr Leu Ser Val Thr Pro Gly
1               5                   10                  15 gat aga gtc ggt ctt tcc tgc agg gcc agt caa agt ctt agc aac tac      96
Asp Arg Val Gly Leu Ser Cys Arg Ala Ser Gln Ser Leu Ser Asn Tyr
            20                  25                  30 cta cac tgg tat caa caa aaa tca cat gag tct cca agg ctt ctc atc     144
Leu His Trp Tyr Gln Gln Lys Ser His Glu Ser Pro Arg Leu Leu Ile
        35                  40                  45 aac tat gct tcc cag tcc atc tct ggg atc ccc tcc agg ttc agt ggc     192
Asn Tyr Ala Ser Gln Ser Ile Ser Gly Ile Pro Ser Arg Phe Ser Gly
    50                  55                  60 agt gga tca ggg aca gat ttc act ctc agt atc aac agt gtg gag act     240
Ser Gly Ser Gly Thr Asp Phe Thr Leu Ser Ile Asn Ser Val Glu Thr
65                  70                  75                  80 gaa gat ttt gga atg tgt ttc tgt caa cag agt aac agc tgg cct ctc     288
Glu Asp Phe Gly Met Cys Phe Cys Gln Gln Ser Asn Ser Trp Pro Leu
                85                  90                  95 acg ttc ggt gct ggg acc aag ctg                                     312
Thr Phe Gly Ala Gly Thr Lys Leu
                100

<210> SEQ ID NO 7
<211> LENGTH: 104
<212> TYPE: PRT
<213> ORGANISM: Mus musculus

<400> SEQUENCE: 7

Asp Ile Glu Leu Thr Gln Ser Pro Ala Thr Leu Ser Val Thr Pro Gly
1               5                   10                  15

Asp Arg Val Gly Leu Ser Cys Arg Ala Ser Gln Ser Leu Ser Asn Tyr
            20                  25                  30

Leu His Trp Tyr Gln Gln Lys Ser His Glu Ser Pro Arg Leu Leu Ile
        35                  40                  45

Asn Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Cys Phe Cys Gln Gln Ser Asn Ser Trp Pro Leu
```

Thr Phe Gly Ala Gly Thr Lys Leu
                    100

<210> SEQ ID NO 8
<211> LENGTH: 6
<212> TYPE: PRT
<213> ORGANISM: Artificial Sequence
<220> FEATURE:
<223> OTHER INFORMATION: 3H9 variable light chain CDR1

<400> SEQUENCE: 8

Gln Ser Leu Ser Asn Tyr
1               5

<210> SEQ ID NO 9
<211> LENGTH: 9
<212> TYPE: PRT
<213> ORGANISM: Artificial Sequence
<220> FEATURE:
<223> OTHER INFORMATION: 3H9 variable light chain CDR3

<400> SEQUENCE: 9

Gln Gln Ser Asn Ser Trp Pro Leu Thr
1               5

<210> SEQ ID NO 10
<211> LENGTH: 360
<212> TYPE: DNA
<213> ORGANISM: Mus musculus
<220> FEATURE:
<221> NAME/KEY: CDS
<222> LOCATION: (1)..(360)
<223> OTHER INFORMATION: variable heavy chain of mononoclonal
      anti-ADAMTS13 antibody 17C7

<400> SEQUENCE: 10

| gag gtg cag ctg gtg gag tct ggg gga gac tta gtg aag tct gga ggg | 48 |
|---|---|
| Glu Val Gln Leu Val Glu Ser Gly Gly Asp Leu Val Lys Ser Gly Gly | |
| 1               5                   10                  15 | |

| tcc ctg aaa ctc tcc tgt gca gcc tct gga ttc att ttc agt aat tat | 96 |
|---|---|
| Ser Leu Lys Leu Ser Cys Ala Ala Ser Gly Phe Ile Phe Ser Asn Tyr | |
|         20                  25                  30 | |

| gcc atg tct tgg gtt cgc cag act ccg gag aag agg ctg gag tgg ggc | 144 |
|---|---|
| Ala Met Ser Trp Val Arg Gln Thr Pro Glu Lys Arg Leu Glu Trp Gly | |
|     35                  40                  45 | |

| gca acc att act act ggt ggt ttt tac acc ttc tat tca gac agt gtg | 192 |
|---|---|
| Ala Thr Ile Thr Thr Gly Gly Phe Tyr Thr Phe Tyr Ser Asp Ser Val | |
| 50                  55                  60 | |

| aag ggt cga ttc acc atc tcc aga gac aat gcc aag aac acc ctg tac | 240 |
|---|---|
| Lys Gly Arg Phe Thr Ile Ser Arg Asp Asn Ala Lys Asn Thr Leu Tyr | |
| 65                  70                  75                  80 | |

| ctg caa atg agt agt ctg agg tct gag gac acg gcc atg tat tac tgt | 288 |
|---|---|
| Leu Gln Met Ser Ser Leu Arg Ser Glu Asp Thr Ala Met Tyr Tyr Cys | |
|                 85                  90                  95 | |

| gca aga cat agg tac gac gat tac tat gct ttg gac tac tgg ggt caa | 336 |
|---|---|
| Ala Arg His Arg Tyr Asp Asp Tyr Tyr Ala Leu Asp Tyr Trp Gly Gln | |
|             100                 105                 110 | |

| gga acc tca gtc acc gtc tcc tca | 360 |
|---|---|
| Gly Thr Ser Val Thr Val Ser Ser | |
|             115                 120 | |

<210> SEQ ID NO 11
<211> LENGTH: 120

```
<212> TYPE: PRT
<213> ORGANISM: Mus musculus

<400> SEQUENCE: 11

Glu Val Gln Leu Val Glu Ser Gly Gly Asp Leu Val Lys Ser Gly Gly
1               5                   10                  15

Ser Leu Lys Leu Ser Cys Ala Ala Ser Gly Phe Ile Phe Ser Asn Tyr
            20                  25                  30

Ala Met Ser Trp Val Arg Gln Thr Pro Glu Lys Arg Leu Glu Trp Gly
        35                  40                  45

Ala Thr Ile Thr Thr Gly Gly Phe Tyr Thr Phe Tyr Ser Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg His Arg Tyr Asp Asp Tyr Tyr Ala Leu Asp Tyr Trp Gly Gln
            100                 105                 110

Gly Thr Ser Val Thr Val Ser Ser
        115                 120

<210> SEQ ID NO 12
<211> LENGTH: 5
<212> TYPE: PRT
<213> ORGANISM: Artificial Sequence
<220> FEATURE:
<223> OTHER INFORMATION: 17C7 variable heavy chain CDR1

<400> SEQUENCE: 12

Asn Tyr Ala Met Ser
1               5

<210> SEQ ID NO 13
<211> LENGTH: 17
<212> TYPE: PRT
<213> ORGANISM: Artificial Sequence
<220> FEATURE:
<223> OTHER INFORMATION: 17C7 variable heavy chain CDR2

<400> SEQUENCE: 13

Thr Ile Thr Thr Gly Gly Phe Tyr Thr Phe Tyr Ser Asp Ser Val Lys
1               5                   10                  15

Gly

<210> SEQ ID NO 14
<211> LENGTH: 11
<212> TYPE: PRT
<213> ORGANISM: Artificial Sequence
<220> FEATURE:
<223> OTHER INFORMATION: 17C7 variable heavy chain CDR3

<400> SEQUENCE: 14

His Arg Tyr Asp Asp Tyr Tyr Ala Leu Asp Tyr
1               5                   10

<210> SEQ ID NO 15
<211> LENGTH: 318
<212> TYPE: DNA
<213> ORGANISM: Mus musculus
<220> FEATURE:
<221> NAME/KEY: CDS
<222> LOCATION: (1)..(318)
<223> OTHER INFORMATION: variable light chain of monoclonal
``` anti-ADAMTS13 antibody 17C7

<400> SEQUENCE: 15

```
gaa aat gtt ctc acc cag tct cca gca atc atg tct aca tct cca ggg      48
Glu Asn Val Leu Thr Gln Ser Pro Ala Ile Met Ser Thr Ser Pro Gly
1               5                   10                  15 gaa aag gtc acc atg acc tgt aat gtc agc tca agt gta agt tac atg      96
Glu Lys Val Thr Met Thr Cys Asn Val Ser Ser Ser Val Ser Tyr Met
            20                  25                  30 cgc tgg ttc cag cag aag tca agc acc tcc ccc aaa cta tgg att tat     144
Arg Trp Phe Gln Gln Lys Ser Ser Thr Ser Pro Lys Leu Trp Ile Tyr
        35                  40                  45 gac aca tcc aaa ctg gct tct gga gtc cca ggt cgc ttc agt ggc agt     192
Asp Thr Ser Lys Leu Ala Ser Gly Val Pro Gly Arg Phe Ser Gly Ser
    50                  55                  60 ggg tct gga cac tct tac tct ctc acg atc agt agc atg gag gct gac     240
Gly Ser Gly His Ser Tyr Ser Leu Thr Ile Ser Ser Met Glu Ala Asp
65                  70                  75                  80 gat gtt gcc act tat tac tgt ttt cag ggg aat ggg tac cca ctc acg     288
Asp Val Ala Thr Tyr Tyr Cys Phe Gln Gly Asn Gly Tyr Pro Leu Thr
                85                  90                  95 ttc ggt gct ggg acc aag ctg gag ctg aaa                             318
Phe Gly Ala Gly Thr Lys Leu Glu Leu Lys
            100                 105
```

<210> SEQ ID NO 16
<211> LENGTH: 106
<212> TYPE: PRT
<213> ORGANISM: Mus musculus

<400> SEQUENCE: 16

```
Glu Asn Val Leu Thr Gln Ser Pro Ala Ile Met Ser Thr Ser Pro Gly
1               5                   10                  15

Glu Lys Val Thr Met Thr Cys Asn Val Ser Ser Ser Val Ser Tyr Met
            20                  25                  30

Arg Trp Phe Gln Gln Lys Ser Ser Thr Ser Pro Lys Leu Trp Ile Tyr
        35                  40                  45

Asp Thr Ser Lys Leu Ala Ser Gly Val Pro Gly Arg Phe Ser Gly Ser
    50                  55                  60

Gly Ser Gly His Ser Tyr Ser Leu Thr Ile Ser Ser Met Glu Ala Asp
65                  70                  75                  80

Asp Val Ala Thr Tyr Tyr Cys Phe Gln Gly Asn Gly Tyr Pro Leu Thr
                85                  90                  95

Phe Gly Ala Gly Thr Lys Leu Glu Leu Lys
            100                 105
```

<210> SEQ ID NO 17
<211> LENGTH: 10
<212> TYPE: PRT
<213> ORGANISM: Artificial Sequence
<220> FEATURE:
<223> OTHER INFORMATION: 17C7 variable light chain CDR1

<400> SEQUENCE: 17

```
Asn Val Ser Ser Ser Val Ser Tyr Met Arg
1               5                   10
```

<210> SEQ ID NO 18
<211> LENGTH: 7
<212> TYPE: PRT
<213> ORGANISM: Artificial Sequence

```
<220> FEATURE:
<223> OTHER INFORMATION: 17C7 variable light chain CDR2

<400> SEQUENCE: 18

Asp Thr Ser Lys Leu Ala Ser
1               5

<210> SEQ ID NO 19
<211> LENGTH: 9
<212> TYPE: PRT
<213> ORGANISM: Artificial Sequence
<220> FEATURE:
<223> OTHER INFORMATION: 17C7 variable light chain CDR3

<400> SEQUENCE: 19

Phe Gln Gly Asn Gly Tyr Pro Leu Thr
1               5

<210> SEQ ID NO 20
<211> LENGTH: 339
<212> TYPE: DNA
<213> ORGANISM: Mus musculus
<220> FEATURE:
<221> NAME/KEY: CDS
<222> LOCATION: (1)..(339)
<223> OTHER INFORMATION: fragment of 3H9 variable heavy chain

<400> SEQUENCE: 20 gac tta gtg aag cct gga ggg tcc ctg aaa ctc tcc tgt gca gcc tct        48
Asp Leu Val Lys Pro Gly Gly Ser Leu Lys Leu Ser Cys Ala Ala Ser
1               5                   10                  15 gga ttc act ttc agt agc tat ggc atg tct tgg gtt cgc cag act cca        96
Gly Phe Thr Phe Ser Ser Tyr Gly Met Ser Trp Val Arg Gln Thr Pro
                20                  25                  30 gac aag agg ctg gag tgg gtc gca acc att agt agt ggt gga act tac        144
Asp Lys Arg Leu Glu Trp Val Ala Thr Ile Ser Ser Gly Gly Thr Tyr
            35                  40                  45 acc tac tat gca gac act gtg aag ggg cga ttc acc atc tcc aga gac        192
Thr Tyr Tyr Ala Asp Thr Val Lys Gly Arg Phe Thr Ile Ser Arg Asp
        50                  55                  60 aat gcc aag aac acc ctg tac ctg caa atg agc agt ctg acg tct gaa        240
Asn Ala Lys Asn Thr Leu Tyr Leu Gln Met Ser Ser Leu Thr Ser Glu
65                  70                  75                  80 gac tca gcc atg ttt tac tgt gca aga cgg gtg gct tgg gac ttc ggt        288
Asp Ser Ala Met Phe Tyr Cys Ala Arg Arg Val Ala Trp Asp Phe Gly
                85                  90                  95 agt acc tac gac tat gct atg gac tac tgg ggc caa ggg acc acg gtc        336
Ser Thr Tyr Asp Tyr Ala Met Asp Tyr Trp Gly Gln Gly Thr Thr Val
                100                 105                 110 acc                                                                    339
Thr

<210> SEQ ID NO 21
<211> LENGTH: 113
<212> TYPE: PRT
<213> ORGANISM: Mus musculus

<400> SEQUENCE: 21

Asp Leu Val Lys Pro Gly Gly Ser Leu Lys Leu Ser Cys Ala Ala Ser
1               5                   10                  15

Gly Phe Thr Phe Ser Ser Tyr Gly Met Ser Trp Val Arg Gln Thr Pro
                20                  25                  30

Asp Lys Arg Leu Glu Trp Val Ala Thr Ile Ser Ser Gly Gly Thr Tyr
```

-continued

```
               35                  40                  45
Thr Tyr Tyr Ala Asp Thr Val Lys Gly Arg Phe Thr Ile Ser Arg Asp
        50                  55                  60

Asn Ala Lys Asn Thr Leu Tyr Leu Gln Met Ser Ser Leu Thr Ser Glu
65                  70                  75                  80

Asp Ser Ala Met Phe Tyr Cys Ala Arg Arg Val Ala Trp Asp Phe Gly
                85                  90                  95

Ser Thr Tyr Asp Tyr Ala Met Asp Tyr Trp Gly Gln Gly Thr Thr Val
                100                 105                 110

Thr
```